United States Patent [19]

Peet et al.

[11] Patent Number: 5,948,886
[45] Date of Patent: Sep. 7, 1999

[54] ACYLATED ENOL DERIVATIVES OF α-KETOESTERS AND α-KETOAMIDES

[75] Inventors: Norton P. Peet, Cincinnati, Ohio; Joseph P. Burkhart, Plainfield, Ind.; Shujaath Mehdi, West Chester, Ohio

[73] Assignee: Hoechst Marion Roussel, Inc., Bridgewater, N.J.

[21] Appl. No.: 08/978,096

[22] Filed: Nov. 25, 1997

Related U.S. Application Data

[63] Continuation of application No. 08/754,081, Nov. 20, 1996, abandoned

[60] Provisional application No. 60/031,083, Dec. 1, 1996.

[51] Int. Cl.[6] .......................................... C07K 5/00
[52] U.S. Cl. ........................ 530/330; 530/331; 514/18; 514/851
[58] Field of Search ................................ 530/330, 331; 514/18, 851

[56] References Cited

U.S. PATENT DOCUMENTS

| | | | |
|---|---|---|---|
| 4,277,395 | 7/1981 | Bey et al. | 260/112.5 R |
| 4,518,528 | 5/1985 | Rasnick | 260/112.512 |
| 4,623,639 | 11/1986 | Hassall et al. | 514/18 |
| 4,629,724 | 12/1986 | Ryono et al. | 514/18 |
| 4,636,489 | 1/1987 | Seemuller et al. | 514/12 |
| 4,643,991 | 2/1987 | Digenis et al. | 514/18 |
| 4,855,303 | 8/1989 | Hoover | 514/18 |
| 4,873,221 | 10/1989 | Trainor | 514/18 |
| 4,880,780 | 11/1989 | Trainor et al. | 514/18 |
| 4,910,190 | 3/1990 | Bergeson et al. | 514/19 |
| 4,935,405 | 6/1990 | Hoover et al. | 514/19 |
| 5,055,450 | 10/1991 | Edwards et al. | 514/19 |
| 5,114,927 | 5/1992 | Schirlin | 514/18 |
| 5,162,307 | 11/1992 | Digenis et al. | 514/19 |
| 5,221,665 | 6/1993 | Skiles et al. | 514/18 |
| 5,478,811 | 12/1995 | Peet et al. | 514/17 |
| 5,496,927 | 3/1996 | Kolb et al. | 530/328 |
| 5,510,333 | 4/1996 | Angelastro et al. | 514/18 |

FOREIGN PATENT DOCUMENTS

| | | |
|---|---|---|
| 0009384 | 9/1979 | European Pat. Off. . |
| 0189305 | 7/1986 | European Pat. Off. . |
| 0204571 | 12/1986 | European Pat. Off. . |
| 0318318 | 5/1989 | European Pat. Off. . |
| 0369391 | 5/1990 | European Pat. Off. . |
| 0410411 | 1/1991 | European Pat. Off. . |
| 0494071 | 7/1992 | European Pat. Off. . |
| 0529568 | 3/1993 | European Pat. Off. . |
| 9113904 | 9/1991 | WIPO . |
| 9115487 | 10/1991 | WIPO . |
| 9212140 | 7/1992 | WIPO . |
| 9215605 | 9/1992 | WIPO . |
| 0509838 | 4/1995 | WIPO . |
| 9533478 | 12/1995 | WIPO . |
| 9533762 | 12/1995 | WIPO . |
| 9533763 | 12/1995 | WIPO . |

OTHER PUBLICATIONS

Skiles et al., J. Med. Chem. 1992, 35, pp. 641–662, Inhibition of Human Leukocyte Elastase (HLE) by N–Substituted Peptidyl Trifluoromethyl Ketones1.

Skiles et al., J. Med. Chem. 1992, 35, pp. 4795–4808, Inhibition of Human Leukocyte Elastase by N–Substituted Peptides Containing alpha, alpha–Difluorostatone Residues at P1.

Williams et al., publication, Biologic Characterization of ICI 200,880 and ICI 200,355, Novel Inhibitors of Human Neutrophil Elastase 1,2.

Kawase et al., Tetrahedron Letters, vol. 34, No. 5, pp. 859–862, 1993, "Unexpected Product from the Dakin–West Reaction of N–Acylprolines using Trifluoroacetic Anhydride: A Novel Access to 5–Trifluoromethyl–oaxzoles".

Kawase et al., J. Chem. Soc., Chem. Commun., 1992, pp. 1076–1077, "Unusual Ring Expansion observed during the Dakin–West Reaction of Tetrahydroisoquinoline–1–carboxlic Acids using Trifluoroacetic Anhydride: an Expedient Synthesis of 3–Benzazepine Derivatives bearing a Trifluoromethyl Group".

Imperiali et al, Biochemistry 25, 3760–3767, (1986).

kiles et al, Journal of Medicinal Chemistry, vol. 35, No. 4, pp. 641–661 (1992).

Repine et al, J Med Chem. 34, pp. 1935–1943 (1991).

Ueda et al, Biochem. J. 265 pp. 539–545 (1990).

Eleventh American Peptide Symposium—Jul. 9–14, 1989.

Sham et al, FEB 05016, vol. 220, No. 2, pp. 299–301 (1987).

Travis et al, Am. Rev. Respir, Dis. 143:1412–1415, (1991).

Petrillo et al, Annual Reports in Medicinal Chemistry 25, pp. 51–60.

Powers et al, Chemical Abstracts, vol. 108:33954r, 1988, Mechanism–based inhibitors of human leukocyte elastase.

Chemical Abstract vol. 111, No. 9, Aug. 28, 1989, Lafuma et al. p. 17.

Chemical Abstract vol. 111, No. 21, Nov. 20, 1989, Galzigna et al, p. 343.

Steinmeyer et al, Forsch./Drug Res. 41, (I) Nr. (1991).

McWherter et al, Biochemistry 28, pp. 5708–5713 (1989).

Reilly et al, Biochemica et Biophysica Acta. 621 pp. 147–157, (1980).

Najajima et al, Journal of Biological Chemistry, vol. 254, pp. 4027–4031 (1979).

Rice et al, Science, vol. 249, pp. 178–181.

Travis, The American Journal of Medicine, vol. 84, Supl. 6A pp. 37–42 (1988).

Peet et al., J. Med. Chem. 33, pp. 394–407 (1990).

Doherty et al, Int. J. Immunopharmac vol. No. 7, pp. 787–795, (1990).

Mehdi et al, Biochemical and Biophysical Research Communications, vol. 166, No. 2, pp. 595–600 (1990).

(List continued on next page.)

Primary Examiner—Cecilia J. Tsang
Assistant Examiner—C. Delacroix-Muirheid
Attorney, Agent, or Firm—Balaram Gupta

[57] ABSTRACT

This invention relates to acylated enol derivatives of α-ketoesters and α-ketoamides. The compounds of this invention are either prodrugs of known elastase inhibitors or are elastase inhibitors in their own right and are useful in the treatment of various inflammatory diseases, including cystic fibrosis and emphysema.

12 Claims, No Drawings

OTHER PUBLICATIONS

Shah et al, Orally Active β–Latham Inhibitors of Human Leukocyte Elastase–1. J. Med Chem, 35, pp. 3745–3754 (1992).

Snider, Eur, J. Respir. 69, suppl 146, 17–35 (1986).

Malech et al, Medical Intelligence vol. 317, No. 11, pp. 687–694.

Fletcher et al, Am Rev Respir Dis 1990, 141:672–677.

Hassall et al, Febs 2444, vol. 183, No. 2, (1985).

Angelastro et al, J. Org. Chem. 54, pp. 3913–3916, (1989).

Angelastro et al, Journal of Medicinal Chemistry, 37, pp. 4538–4553 (1994).

Angelastro et al, Bioorganic & Medicinal Chemistry Letters, vol. 3, No. 4, pp. 525–530 (1993).

Mehdi, Bioorganic Chemistry, 21, pp. 249–259 (1993).

Angelastro et al., Tetrahedron Letters, vol. 33, No. 23, pp. 3265–3268 (1992).

Burkhart et al., Tetrahedron Letters, vol. 31, No. 10, pp. 1385–1388 (1990).

Angelastro et al, Bioorganic & Medicinal Chemistry Letters, vol. 2, No. 10, pp. 1235–1238 (1992).

J. Med. Chem. 33, pp. 11–13 (1990) Communications to the Editor.

Bundgaard, Hans, "Design of Bioreversible Drug Derivatives and the Utility of the Double Prodrug Concept", Bioreversible Carriers In Drug Design Theory and Application, Chapter 2, pp. 62–65.

Janusz, M. et al, J. Immonol. (1991), vol. 146, pp. 3922–3928.

Janusz, M. et al, J. Pharmacol. Exp. Ther., (1995), vol. 275, pp. 1233–1238.

Zhaozhao Li et al, J. of Medicinal Chemistry, vol. 36, No. 22, pp. 3742–3480, Oct. 29, 1993.

Isabel Charles et al, J. of the Chemical Society, Perkin Transactions 1. No. 5, pp. 1139–1146, May 1980.

Burkhart et al., *J. Med. Chem.,* 38, 223–233, 1995.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:1:

Xaa Xaa Xaa Xaa
   1

(2) INFORMATION FOR SEQ ID NO:2:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:2:

Xaa Xaa Xaa Xaa
   1

(2) INFORMATION FOR SEQ ID NO:3:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:3:

Xaa Xaa Xaa Xaa
   1

(2) INFORMATION FOR SEQ ID NO:4:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:4:

Xaa Xaa Xaa Xaa
   1

(2) INFORMATION FOR SEQ ID NO:5:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:5:

Xaa Xaa Xaa Xaa

1

(2) INFORMATION FOR SEQ ID NO:6:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:6:

Ala Ala Pro Xaa
    1

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:7:

Pro Ala Pro Xaa
    1

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:8:

Ala Ala Pro Xaa
    1

(2) INFORMATION FOR SEQ ID NO:9:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:9:

Ala Ala Pro Xaa
    1

(2) INFORMATION FOR SEQ ID NO:10:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:10:

Ala Ala Pro Xaa

ACYLATED ENOL DERIVATIVES OF α-KETOESTERS AND α-KETOAMIDES

This is a continuation of application Ser. No. 08/754,081 filed Nov. 20, 1996, now abandoned, which claims the benefit of U.S. Provisional Application No. 60/031,083, filed Dec. 1, 1996.

BACKGROUND OF THE INVENTION

This invention relates to acylated enol derivatives of α-ketoesters and α-ketoamides which are either elastase inhibitors or are prodrugs of elastase inhibitors, useful for a variety of physiological and end-use applications.

Human neutrophil elastase has been implicated as an agent contributing to the tissue destruction associated with a number of inflammatory diseases such as chronic bronchitis, cystic fibrosis, and rheumatoid arthritis. J. L. Malech and J. I. Gallin, *New Engl. J. Med.*, 317(11), 687 (1987). Elastase possesses a broad range of proteolytic activity against a number of connective tissue macromolecules including elastin, fibronectin, collagen, and proteoglycan. The presence of the enzyme elastase may contribute to the pathology of these diseases.

Normal plasma contains large quantities of protease inhibitors that control a variety of enzymes involved in connective tissue turnover and inflammation. For example, α-1-proteinase inhibitor (α-1-PI) is a serine protease inhibitor that blocks the activity of elastase. α-1-PI has received considerable interest because reduction in plasma levels to less than 15% of normal is associated with the early development of emphysema.

In addition to plasma derived protease inhibitors, secretory fluids, including bronchial, nasal, cervical mucus, and seminal fluid contain an endogenous protease inhibitor called secretory leukoprotease inhibitor (SLPI) that can inactivate elastase and is believed to play an important role in maintaining the integrity of the epithelium in the presence of inflammatory cell proteases. In certain pathological states α-1-PI and SLPI are inactivated by neutrophil oxidative mechanisms allowing the neutrophil proteases to function in an essentially inhibitor-free environment. For example, bronchial lavage fluids from patients with adult respiratory distress syndrome (ARDS) have been found to contain active elastase and α-1-PI that had been inactivated by oxidation.

In addition to oxidative mechanisms, neutrophils possess non-oxidative mechanisms for eluding inhibition by antiproteases. Neutrophils from patients with chronic granulomatous disease are capable of degrading endothelial cell matrices in the presence of excess α-1-PI. There is considerable in vitro evidence that stimulated neutrophils can tightly bind to their substrates such that serum antiproteases are effectively excluded from the microenvironment of tight cell-substrate contact. The influx of large numbers of neutrophils to an inflammatory site may result in considerable tissue damage due to the proteolysis that occurs in this region.

Applicants have previously determined that elastase is one of the primary neutrophil proteases responsible for cartilage matrix degeneration as measured by the ability of neutrophil lysate, purified elastase and stimulated neutrophils to degrade cartilage matrix proteoglycan. Furthermore, various kinds of peptide derivatives useful as elastase inhibitors, exerting valuable pharmacological activities, are known in the art. For example, Angelastro, M. R. et al. *J. Med. Chem.*, 37, 4538 (1994) and European Patent Application OPI No. 0529568, inventors Peet et al., with a publication date of Mar. 3, 1993 disclose that various peptides such as valylprolylvalyl pentafluoroethyl ketones with different N-protecting groups are inhibitors of human neutrophil elastase (HNE) in vitro and in vivo and are also orally active in HNE-induced rat and hamster lung hemorrhage models.

Moreover, the art discloses that a number of different amino acid moieties are permitted at the $P_1$, $P_3$, $P_4$ sites of the elastase inhibitor and that a number of N-protecting groups may be substituted while still maintaining enzyme inhibitory activity, although oral activity is noted for only some N-protecting groups. For example, Skiles, J. W. et al., *J. Med. Chem.*, 35, 641 (1992) disclose a number of tripeptide elastase inhibitors possessing trifluoromethyl or aryl ketone residues at $P_1$ and N-substituted glycine residues at $P_2$. It is demonstrated that as the substituent on the $P_2$-glycine is increased in size and lipophilicity, ranging from H, $CH_3$, cyclopentyl, exo-norbornyl, 2-indanyl, cycloheptyl, cyclooctyl, and also piperidinyl, benzyl, 3,4-dimethyoxypenethyl, tetrahydrofufuryl and furfuryl, no dramatic change in in vitro potency is observed.

Likewise, U.S. Pat. No. 4,910,190, issued Mar. 20, 1990 to Bergeson et al. and U.S. Pat. No. 5,194,588, issued Mar. 16, 1993 to Edwards et al. and European Patent Appl. Publ. No. 0195212, inventors Michael Kolb et al., published Sep. 24, 1986, teach that a number of alkyl and substituted alkyl groups are allowable as the side chain groups of the amino acids at the $P_3$ and $P_4$ positions. Moreover, elastase inhibitors containing typical N-protecting groups such as acetyl, succinyl, t-butyloxy-carbonyl, carbobenzyloxy, 4-((4-chlorophenyl)sulfonylamino-carbonyl)phenylcarbonyl, and the like have been specifically disclosed.

Several analogs of N-[4-(4-morpholinylcarbonyl)-benzoyl]-L-valyl-N-[3,3,4,4,4-pentafluoro-1-(1-methylethyl)-2-oxobutyl]-L-prolinamide in which the chiral center of the $P_1$ residue has been eliminated are disclosed as prodrugs of elastase inhibitors by Burkhart, J. P. et al., *J. Med. Chem.*, 38, 223 (1995). Applicants have recently discovered acylated enol derivatives of known nonfluorinated elastase inhibitors which are useful as prodrugs of elastase inhibitors or are elastase inhibitors in their own right.

SUMMARY OF THE INVENTION

The present invention relates to compounds of the formulae

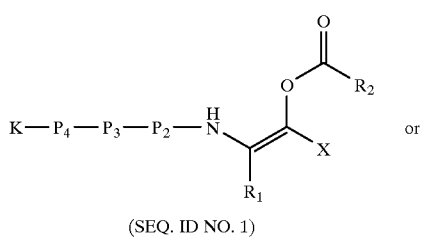

(SEQ. ID NO. 1)

-continued

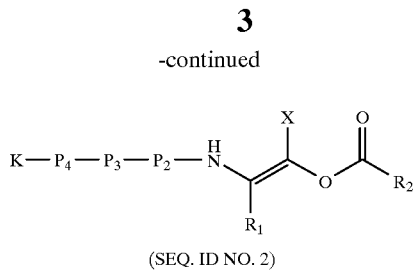

(SEQ. ID NO. 2)

wherein

R₁ is $(C_1-C_4)$alkyl;

R₂ is $(C_1-C_4)$alkyl, phenyl, benzyl, cyclohexyl or cyclohexylmethyl;

x is —$CO_2R_3$ or —$CONHR_3'$ wherein R₃ is $(C_1-C_4)$alkyl, phenyl, benzyl, cyclohexyl or cyclohexylmethyl and R₃' is hydrogen, $(C_1-C_4)$alkyl, phenyl, benzyl, cyclohexyl or cyclohexylmethyl;

P₂ Gly or Ala where the nitrogen of the α-amino group is optionally substituted with an R group where R is $(C_1-C_6)$ alkyl, $(C_3-C_{12})$ cycloalkyl, $(C_3-C_{12})$ cycloalkyl $(C_1-C_6)$alkyl, $(C_4-C_{11})$bicycloalkyl, $(C_4-C_{11})$bicycloalkyl$(C_1-C_6)$alkyl, $(C_6-C_{10})$aryl, $(C_6-C_{10})$aryl$(C_1-C_6)$alkyl, $(C_3-C_7)$heterocycloalkyl, $(C_3-C_7)$heterocycloalkyl$(C_1-C_6)$alkyl, $(C_5-C_9)$heteroaryl, $(C_5-C_9)$heteroaryl$(C_1-C_6)$alkyl, fused $(C_6-C_{10})$aryl$(C_3-C_{12})$cycloalkyl, fused $(C_6-C_{10})$aryl $(C_3-C_{12})$cycloalkyl$(C_1-C_6)$alkyl, fused $(C_5-C_9)$ heteroaryl $(C_3-C_{12})$cycloalkyl, or fused $(C_5-C_9)$ heteroaryl$(C_3-C_{12})$cycloalkyl$(C_1-C_6)$alkyl, or P₂ is Pro, Aze, Ind, Tic, Pip, Tca, Pro(4-OBzl), Pro(4-OAc), Pro(4-OH);

P₃ is Ala, bAla, Leu, Ile, Nle, Val, Nva, Lys or bVal;

P₄ is Ala, bAla, Val, Nva, bVal, Pro or is deleted;

K is hydrogen, acetyl, succinyl, benzoyl, t-butyloxycarbonyl, carbobenzyloxy, dansyl, isovaleryl, methoxysuccinyl, 1-adamantanesulphonyl, 1-adamantaneacetyl, 2-carboxybenzoyl, —C(O)N(CH₃)₂, 4-((chlorophenyl)sulfonylaminocarbonyl) phenylcarbonyl, 4-((4-bromophenyl)sulfonylaminocarbonyl)phenylcarbonyl, 4-(sulfonylaminocarbonyl)phenylcarbonyl or is a group of the formulae

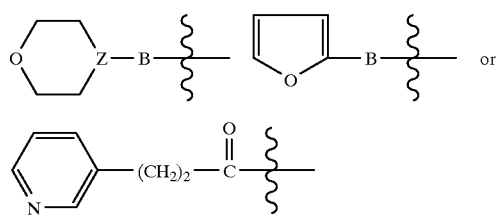

wherein Z is N or CH, B is a group of the formulae

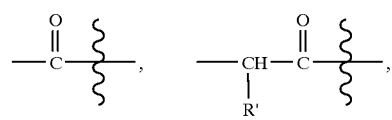

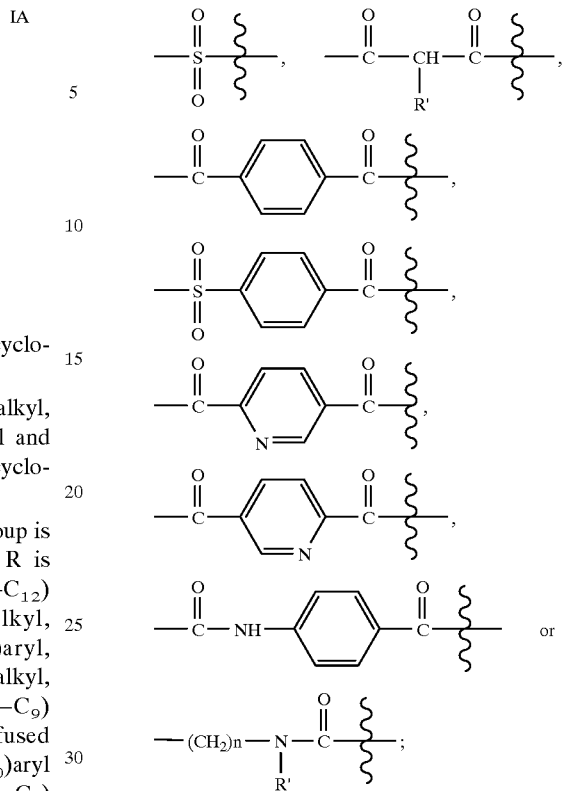

(the wavy line being the attachment to the rest of the molecule, e.g. not to Z)

R' is a hydrogen or a $(C_1-C_4)$alkyl group;

n is zero or the integers 1 or 2;

or a hydrate or a pharmaceutically acceptable salt thereof useful as prodrugs of known elastase inhibitors or inhibit elastase in their present form. The compounds of formulae I or IA thus either exhibit an anti-inflammatory effect useful in the treatment of emphysema, cystic fibrosis, adult respiratory distress syndrome, septicemia, disseminated intravascular coagulation, gout, rheumatoid arthritis, chronic bronchitis and inflammatory bowel disease; or are prodrugs of compounds which exhibit such effects.

DETAILED DESCRIPTION OF THE INVENTION

As used herein the term "$(C_1-C_4)$alkyl" means a straight or branched alkyl group of from 1 to 4 carbon atoms, such as, methyl, ethyl, n-propyl, isopropyl, n-butyl, isobutyl and the like. Similarly, the term "$(C_1-C_6)$alkyl" means a straight or branched alkyl group of from 1 to 6 carbon atoms, such as, methyl, ethyl, n-propyl, isopropyl, n-butyl, n-pentyl, sec-pentyl, iso-pentyl and n-hexyl. The term "$(C_3-C_{12})$ cycloalkyl" means a cyclic alkyl group consisting of a 3 to 12 member ring which can be substituted by a lower alkyl group, for example, cyclopropyl, cyclobutyl, cyclopentyl, cyclohexyl, 4-methylcyclohexyl, 4-ethylcyclohexyl, cycloheptyl, and cyclooctyl. The term "$(C_3-C_{12})$ cycloalkyl $(C_1-C_6)$alkyl" means a $(C_1-C_6)$alkyl group substituted by a $(C_3-C_{12})$cycloalkyl group, such as a cyclohexylmethyl or cyclopentylethyl group. The term "$(C_4-C_{11})$bicycloalkyl" means an alkyl group containing one pair of bridgehead carbon atoms, such as 2-bicyclo[1.1.0]butyl, 2-bicyclo

[2.2.1]hexyl, and 1-bicyclo[2.2.2]octane. The term "($C_4$–$C_{11}$)bicycloalkyl($C_1$–$C_6$)alkyl" means a ($C_1$–$C_6$)alkyl substituted by a ($C_4$–$C_{11}$)bicycloalkyl, such as 2-bicyclohexylmethyl. The term "($C_6$–$C_{10}$)aryl" means a cyclic, aromatic assemblage of conjugated carbon atoms, for example, phenyl, 1-naphthyl, and 2-naphthyl. The term "($C_6$–$C_{10}$)aryl($C_1$–$C_6$)alkyl" means a ($C_1$–$C_6$)alkyl substituted by a ($C_6$–$C_{10}$)aryl, such as benzyl, phenethyl, and 1-naphthylmethyl. The term "($C_3$–$C_7$)heterocycloalkyl" means a nonaromatic, carbon containing cyclic group which contains from 1 to 3 heteroatoms selected from oxygen, nitrogen and sulfur, such as morpholinyl and piperidinyl. The term "($C_3$–$C_7$) heterocycloalkyl($C_1$–$C_6$)alkyl" means a ($C_1$–$C_6$)alkyl group substituted by a ($C_3$–$C_7$) heterocycloalkyl group, for example, morpholinomethyl. The term "($C_5$–$C_9$)heteroaryl" means a cyclic or bicyclic, aromatic assemblage of conjugated carbon atoms and from 1 to 3 nitrogen, oxygen, and sulfur atoms, for example, pyridinyl, 2-quinoxalinyl, and quinolinyl. The term "($C_5$–$C_9$) heteroaryl ($C_1$–$C_6$) alkyl" means ($C_1$–$C_6$)alkyl group substituted by a ($C_5$–$C_9$) heteroaryl group, such as, 3-quinolinylmethyl. The term "fused ($C_6$–$C_{10}$) aryl ($C_{3-12}$) cycloalkyl" means a "($C_3$–$C_{12}$)cycloalkyl" group which has one or more sides shared with a "($C_6$–$C_{10}$)aryl" group and can, for example, include groups derived by the fusion of benzene and cyclopentane, that is 2-indanyl. The term "fused ($C_6$–$C_{10}$)aryl($C_3$–$C_{12}$)cycloalkyl($C_1$–$C_6$)alkyl" means a ($C_1$–$C_6$)alkyl substituted by a fused ($C_6$–$C_{10}$)aryl ($C_3$–$C_{12}$)cycloalkyl group. The term "fused ($C_5$–$C_9$) heteroaryl ($C_3$–$C_8$)cycloalkyl" means a ($C_5$–$C_9$)heteroaryl group which has one or more sides shared with a ($C_3$–$C_8$) cycloalkyl group and can, for example, include groups derived by the fusion of cyclohexane and pyridine, that is tetrahydroquinoline. Finally the term "fused ($C_5$–$C_9$) heteroaryl($C_3$–$C_8$)cycloalkyl($C_1$–$C_6$)alkyl" means a ($C_1$–$C_6$)alkyl substituted by a fused ($C_5$–$C_9$)heteroaryl ($C_3$–$C_8$)cycloalkyl group.

The term "stereoisomers" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereomers). For amino acids, the designations L/D, or R/S can be used as described in IUPAC-IUB Joint Commission on Biochemical Nomenclature, *Eur. J. Biochem.* 138: 9–37 (1984).

The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicylic, hydroxyethanesulfonic, ethylenesulfonic, halobenzenesulfonic, toluenesulfonic, naphthalenesulfonic, methanesulfonic, sulfanilic, and the like.

Each α-amino acid has a characteristic "R-group", the R-group being the side chain, or residue, attached to the α-carbon atom of the α-amino acid. For example, the R-group side chain for glycine is hydrogen, for alanine it is methyl, for valine it is isopropyl. For the specific R-groups or side chains of the α-amino acids see A. L. Lehninger's text on Biochemistry.

Unless otherwise stated, the α-amino acids of these peptidase substrate analogs are preferably in their L-configuration; however, applicants contemplate that the amino acids of the formula 1 compounds can be of either the D- or L-configurations or can be mixtures of the D- and L-isomers, including the racemic mixture. The recognized abbreviations for the α-amino acids are set forth in Table I.

TABLE 1

| Amino Acid | Symbol |
|---|---|
| Alanine | Ala |
| Glycine | Gly |
| Isoleucine | Ile |
| Leucine | Leu |
| Lysine | Lys |
| Phenylalanine | Phe |
| Proline | Pro |
| Tryptophan | Trp |
| Tyrosine | Tyr |
| Valine | Val |
| Norvaline | Nva |
| Norleucine | Nle |
| 2-Indolinecarboxylic acid | Ind |
| beta-Alanine | bAla |
| Methionine | Met |
| Azetidine carboxylic acid | Aze |
| 4-Acetoxyproline | Pro (4-OAc) |
| 4-Benzyloxyproline | Pro (4-OBzl) |
| 4-Hydroxyproline | Pro (4-OH) |
| Pipecolinic acid | Pip |
| Thiazolidine-4-carboxylic acid | Tca |
| 1,2,3,4-Tetrahydro-3-isoquinoline carboxylic acid | Tic |
| beta-Valine | bVal |

In general, the compounds of Formulae I and IA may be prepared using standard chemical reactions analogously known in the art and as depicted in scheme A, wherein the terms K, $P_4$, $P_3$, $P_2$, $R_1$, $R_2$ and X are as defined in Formulae I and IA.

Scheme A

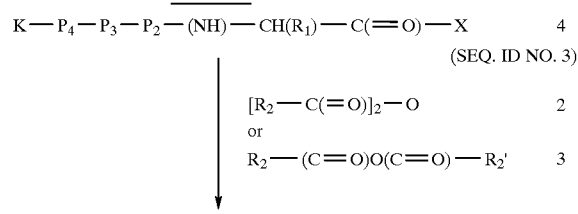

-continued

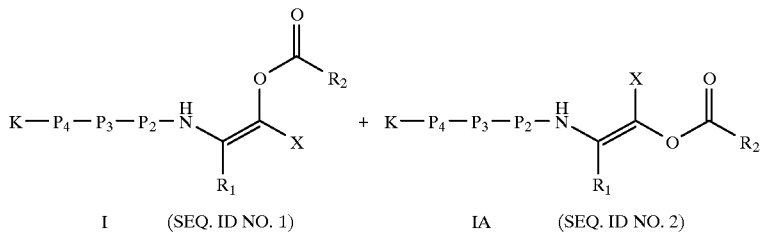

I (SEQ. ID NO. 1)   IA (SEQ. ID NO. 2)

Generally, the acylated enols of formulae I and IA may be formed by reacting the peptide of formula 4 with a suitable symmetrical anhydride 2 or a suitable mixed anhydride 3 (wherein $R_2'$ and $R_2$ are different but are both $R_2$ groups as defined above) in the presence of an amine base, such as the tertiary amines triethylamine and N-methyl-morpholine or aromatic amines such as 4-dimethylamino-pyridine as well as picolines, collidines and pyridine. The reactants may be contacted in a suitable organic solvent such as acetonitrile, methylene chloride, and the like. The reaction is typically carried out over a period of time ranging from about 30 minutes to about 48 hours at a temperature within the range of from about $-40°$ C. to about $85°$ C. Generally, temperatures below $0°$ C. provide high ratios of IA to I and IA may be isolated in its pure form by chromatography or recrystallization. Generally, reaction temperatures greater than $0°$ C. provide increasing ratios of I to IA and I may be isolated by chromatography or recrystallization.

Alternatively, the acylated enols of formulae I and IA may be formed by reacting the peptide of formula 4 with a suitable acid halide of the formula $R_2$—C(=O)X (X=F, Cl, Br, I) in the presence of a weakly basic amine such as the picolines, collidines or pyridine.

Compounds of formula 4 are disclosed in European Patent Appl. Publ. No. 0195212, inventors Michael Kolb et al., with a publication date of Sep. 24, 1986 and in Peet, N. P. et al., *J. Med. Chem.*, 33: 394–407 (1990), both references hereby incorporated by reference as if fully set forth.

Those compounds of formula 4 defined herein, but not disclosed in European Patent Appl. Publ. No. 0195212 or Peet, N. P. et al., *J. Med. Chem.*, 33: 394–407 (1990), may be prepared by the following synthetic procedures which are well known and appreciated by one of ordinary skill in the art.

In general, all of the compounds of formula 4 may be prepared using standard chemical reactions analogously known in the art and as depicted in Scheme B.

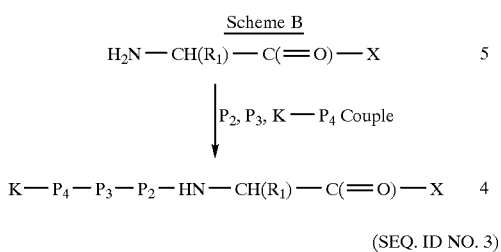

Scheme B (SEQ. ID NO. 3)

Scheme B provides a general synthetic scheme for preparing the compounds of formula 4.

The $P_2$, $P_3$ and K-$P_4$ groups can be linked to the free amino group of the amino acid derivative of structure 5. Note that structure 5 represents the $P_1$ moiety wherein the free carboxylic acid group has been substituted with an "X" moiety as defined above. The $P_2$, $P_3$ and K-$P_4$ can be linked to the unprotected, free amino compound ($P_1$-X) by well known peptide coupling techniques. Furthermore, the $P_1$, $P_2$, $P_3$ and K-$P_4$ groups may be linked together in any order as long as the final compound is K-$P_4$-$P_3$-$P_2$-$P_1$-X. For example, K-$P_4$ can be linked to $P_3$ to give K-$P_4$-$P_3$ which is linked to $P_2$-$P_1$-X; or K-$P_4$ linked to $P_3$-$P_2$ then linked to an appropriately C-terminal protected $P_1$ and the C-terminal protecting group converted to X.

Generally, peptides are elongated by deprotecting the α-amine of the N-terminal residue and coupling the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme B, or by condensation of fragments (two to several amino acids), or combination of both processes, or by solid phase peptide synthesis according to the method originally described by Merrifield, *J. Am. Chem. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers contain a group which will react with the carboxylic acid group to form a bond which is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated.

Alternatively, compounds of the invention can be synthesized using automated peptide synthesizing equipment. In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis" Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The α-carboxyl group of the C-terminal residue is usually, but does not have to be, protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino group of each amino acid to be coupled to the growing peptide chain must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropyl-methoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Boc or Fmoc, preferably Boc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or ethyl acetate. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acid bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group.

For example, when Boc is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine; and benzyl (Bzl) ether can be used to protect the hydroxy containing side chains of amino acids such as Ser or Thr.

When Fmoc is chosen for the α-amine protection usually tert-butyl based protecting groups are acceptable. For instance, Boc can be used for lysine, tert-butyl ether for serine and threonine and tert-butyl ester for glutamic acid.

Once the elongation of the peptide is completed all of the protecting groups are removed. When a solution phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acidic reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using a solution of trifluoroacetic acid and various additives such as anisole, etc.

Alternatively, the compounds of formula 4 may be prepared using standard chemical reactions analogously known in the art and as depicted in Scheme C.

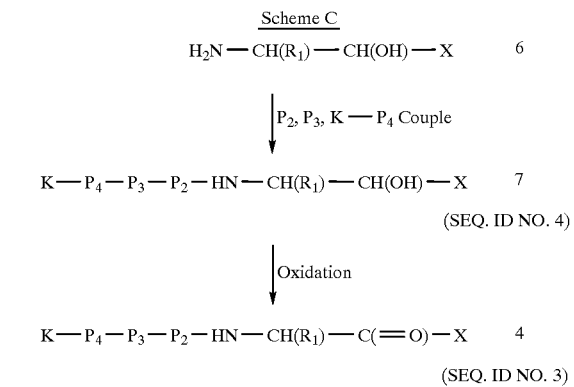

Scheme C provides an alternative general synthetic scheme for preparing the compounds of formula 4.

The $P_2$, $P_3$ and $K$-$P_4$ groups can be linked to the free amino group of the amino alcohol derivative of structure 6 as described previously in Scheme B to give the peptido alcohol of structure 7.

The alcohol functionality of the peptido alcohol of structure 7 is then oxidized by techniques and procedures well known and appreciated by one of ordinary skill in the art, such as a Swern Oxidation using oxalyl chloride and dimethylsulfoxide, to give the compounds of formula 4.

Starting materials for use in Schemes B and C are readily available to one of ordinary skill in the art. For example, amino acids $P_2$, $P_3$ and $K$-$P_4$ wherein K is hydrogen are commercially available. In addition, amino protecting group K wherein K is acetyl, succinyl, benzoyl, t-butyloxycarbonyl, carbobenzyloxy, dansyl, isovaleryl, methoxysuccinyl, 1-adamantanesulphonyl, 1-adamantaneacetyl, 2-carboxybenzoyl, 4-((chlorophenyl)

sulfonylaminocarbonyl)-phenylcarbonyl, 4-((4-bromophenyl)sulfonylaminocarbonyl)-phenylcarbonyl, and 4-(sulfonylaminocarbonyl)phenylcarbonyl are described in European Patent Appl. Publ. No. 363 284, published Apr. 11, 1990 and U.S. Pat. No. 4,910,190, issued Mar. 20, 1990, both references hereby incorporated by reference as if fully set forth. Moreover, K groups wherein K is —C(O)N(CH$_3$)$_2$, or is a group of the formulae

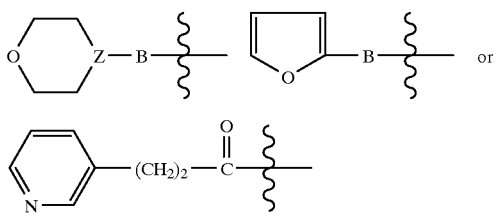

wherein Z is N or CH, B is a group of the formulae

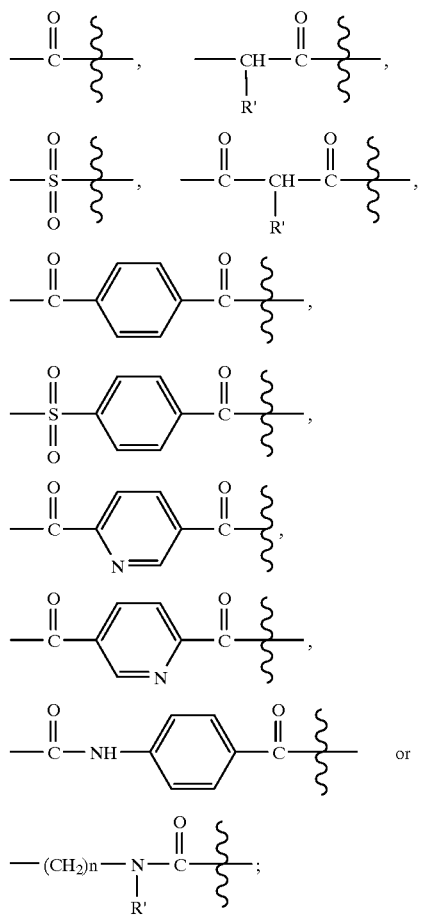

R' is a hydrogen or a (C$_1$–C$_4$)alkyl group; n is zero or the integers 1 or 2; X is N or CH; are described in Angelastro, M. R. et al. *J. Med. Chem.*, 37: 4538–4553 (1994) and European Patent Appl. Publ. No. 529 568, published Mar. 3, 1993, and PCT International Publ. No. WO 95/09838, published Apr. 13, 1995; all three references hereby incorporated by reference as if fully set forth. Synthetic procedures for converting said K groups into K-P$_4$ substituents are well known and appreciated by one of ordinary skill in the art.

Starting amino compounds of formula 5 are readily available to one of ordinary skill in the art. For example, certain protected amino compounds of formula 5 wherein X is as defined above are described in European Patent Appl. Publ. No. 195 212, published Sep. 24, 1986. Said publication is incorporated herein by reference as if fully set forth.

In addition, other starting materials for use in Schemes B and C may be prepared by the following synthetic procedures which are well known and appreciated by one of ordinary skill in the art.

The procedure for preparing the substituted amino acids K-P$_4$ where K is

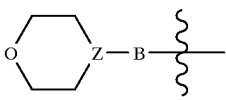

wherein

B is a —C(=O)— group is outlined in Scheme D wherein P$_4$ and Z are as previously defined or are the functional equivalents of these groups.

Scheme D

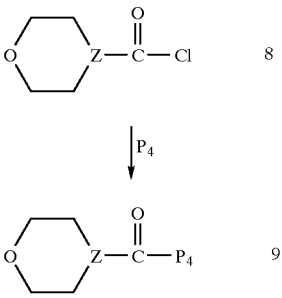

Specifically, the amino acids K-P$_4$ wherein K is

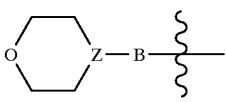

wherein

B is a —C(=O)— are prepared by coupling of the amino acid K-P$_4$ wherein K is hydrogen with an acid chloride of structure 8 in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride of structure 8, to a solution of the amino acid K-P$_4$ wherein K is hydrogen. The solvent can be any suitable solvent, for example, petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The N-protected amino acids K-P$_4$ wherein K is wherein B is a —C(=O)— can be isolated from the reaction mixture by any appropriate techniques such as by chromatography on silica gel.

The substituted amino acids K-P$_4$ wherein K is wherein

B is other than a —C(=O)— group can be prepared analogously, merely by substituting the appropriate intermediate wherein B is other than a —C(=O)— group and A is Cl or OH (the corresponding acid, acid chloride or sulphonyl chloride) for the compound of structure 8 in Scheme D.

The acid chloride of structure 8 and the appropriate intermediate of formula wherein B is other than a —C(=O)— group and A is Cl or OH are commercially available or may be readily prepared by techniques and procedures well known and appreciated by one of ordinary skill in the art.

For example, the appropriate intermediate of formula may be prepared as outlined in Scheme E wherein all substituents are as previously defined.

Scheme E

Scheme E provides a general synthetic procedure for preparing the appropriate intermediates of formula wherein Z is as previously defined.

In step a, the carboxylic acid functionality of the appropriate 2,5-pyridinedicarboxylic acid, 2-methyl ester 10 (*Nippon Kagaku Zasshi,* 1967, 88, 563) is converted to its acid chloride using techniques and procedures well known and appreciated by one of ordinary skill in the art, such as thionyl chloride, to give the corresponding 6-carbomethoxynicotinoyl chloride 11.

In step b, the acid chloride 11 is amidated with morpholine 12 by techniques and procedures well known and appreciated by one of ordinary skill in the art to give the corresponding 5-(morpholine-4-carbonyl)-2-pyridinecarboxylic acid, methyl ester 13.

In step c, the methyl ester functionality of 13 is hydrolyzed by techniques and procedures well known and appreciated by one of ordinary skill in the art, with for example, lithium hydroxide in methanol, to give 5-(morpholine-4-carbonyl)-2-pyridinecarboxylic acid 14.

In addition, the appropriate intermediate of formula may be prepared as outlined in Scheme F wherein all substituents are as previously defined.

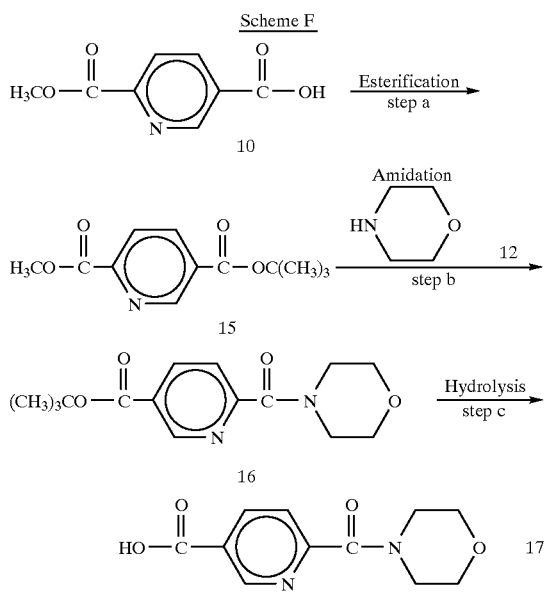

Scheme F

Scheme F provides a general synthetic procedure for preparing the appropriate intermediates of formula

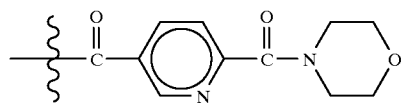

wherein
Z is as previously defined.

In step a, the free carboxylic acid functionality of 2,5-pyridinedicarboxylic acid, 2-methyl ester 10 (*Nippon Kagaku Zasshi*, 1967, 88, 563) is converted to its t-butyl ester using techniques and procedures well known and appreciated by one of ordinary skill in the art, such as the t-butyl alcohol adduct of dicyclohexylcarbodiimide (*Synthesis*, 1979, 570), to give the corresponding 2,5-pyridinedicarboxylic acid, 2-methyl ester, 5-t-butyl ester 15.

For example, the 2,5-pyridinedicarboxylic acid, 2-methyl ester 10 is combined with a molar excess of the t-butyl alcohol adduct of dicyclohexylcarbodiimide in an appropriate organic solvent, such as methylene chloride. The reaction is typically conducted at a temperature range of from 0° C. to room temperature and for a period of time ranging from 2–24 hours. The 2,5-pyridinedicarboxylic acid, 2-methyl ester, 5-t-butyl ester 15 is isolated from the reaction mixture by standard extractive methods as is known in the art and may be purified by crystallization.

In Step b, the methyl ester functionality of 15 is amidated with morpholine 12 to give the corresponding 6-(morpholine-4-carbonyl)nicotinic acid, t-butyl ester 16.

For example, the 2,5-pyridinedicarboxylic acid, 2-methyl ester, 5-t-butyl ester 15 is contacted with a molar excess of morpholine in an appropriate organic solvent, such as tetrahydrofuran. The reaction is typically conducted at a temperature range of from room temperature to reflux and for a period of time ranging from 5 hours to 3 days. The 6-(morpholine-4-carbonyl)nicotinic acid, t-butyl ester 16 is isolated from the reaction mixture by standard extractive methods as is known in the art and may be purified by crystallization.

In step c, the t-butyl ester functionality of 16 is hydrolyzed, with for example, HCl in nitromethane, to give the corresponding 6-(morpholine-4-carbonyl)nicotinic acid 17.

In general, the compounds of formulae 4 or 5 may be prepared using standard chemical reactions analogously known in the art. Compounds of formulae 5 or 6 wherein X is —$CO_2R_3$, that is, where the compounds are α-keto esters, may be prepared as described by Angelastro, M. R. et al., *J. Med. Chem.*, 33, 11 (1990); Peet, N. P. et al., *J. Med. Chem.*, 33, 394 (1990); Mehdi, S. et al., *Biochem. Biophys. Res. Comm.*, 166, 595 (1990) and European Patent Application OPI No. 0195212, inventors Michael Kolb et al., with a publication date of Sep. 24, 1986, all four references hereby incorporated by reference as if fully set forth.

The compounds of formulae 4 or 5 wherein X is —$CONHR_{31}$ that is, where the compounds are α-keto amides, may be prepared as described in PCT International Publ. No. WO 95/09838, published Apr. 13, 1995, hereby incorporated by reference as if fully set forth. The compounds of formulae 4 or 5 wherein X is —$CONHR_3$, may also be prepared following the procedure described in Scheme G. All the substituents, unless otherwise indicated, are as previously defined. The reagents and starting materials are readily available to one of ordinary skill in the art.

Scheme G

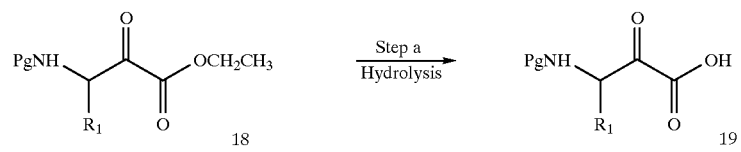

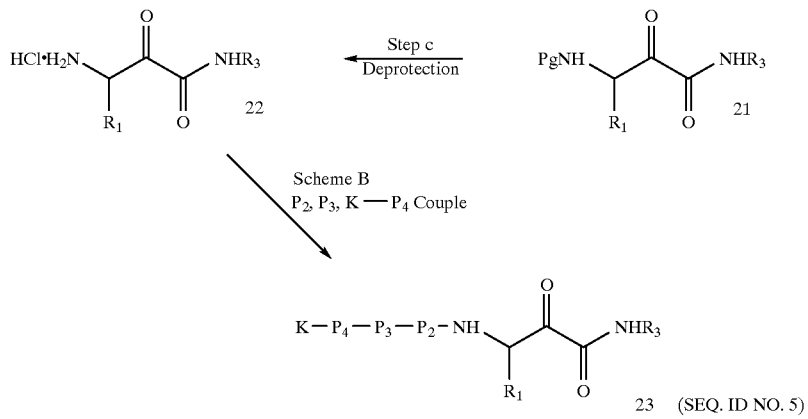

The required α-keto ester 18 starting material may be prepared as described by Angelastro, M. R. et al., *J. Med. Chem.*, 33, 11 (1990); Peet, N. P. et al., *J. Med. Chem.*, 33, 394 (1990); and European Patent Application OPI No. 0195212, inventors Michael Kolb et al., with a publication date of Sep. 24, 1986. The term "Pg" refers to a suitable protecting group as more fully described previously.

In Scheme G, step a, the α-keto ester 18 is selectively hydrolyzed to the α-keto acid 19 by treatment with a suitable base.

For example, the appropriately substituted α-keto ester 18 is dissolved in a suitable solvent mixture, such as methanol:water (50:50) and treated with an equivalent of a suitable base, such as lithium hydroxide. The reaction is stirred at a temperature of about 0° C. to 30° C. for about 1 to 10 hours. The α-keto acid 19 is then isolated by extractive techniques well known in the art. For example, the reaction is diluted with a suitable organic solvent, such as ethyl acetate and an equal volume of water. The layers are separated. The aqueous layer is acidified with dilute hydrochloric acid and extracted with a suitable organic solvent, such as ethyl acetate. The combined organic extracts are dried over anhydrous magnesium sulfate, filtered and concentrated under vacuum to provide the α-keto acid 19.

In Scheme G, step b, the α-keto acid 19 is coupled with a primary amine 20 under conditions well known in the art to provide the desired α-keto amide 21.

For example, the appropriately substituted α-keto acid 19 is dissolved in a suitable organic solvent, such as methylene chloride. The solution is then treated with one equivalent of 1-hydroxybenzotriazole, one equivalent of diisopropylethylamine and an excess of a primary amine 20. An equivalent of 1-(3-dimethylaminopropyl)-3-ethylcarbodiimide hydrochloride is added and the reaction is stirred at a temperature of about 0° C. to 25° C. for about 2 to 10 hours. The product is then isolated by techniques well known in the art. For example, the reaction is diluted with ethyl acetate, rinsed with cold 0.5 N hydrochloric acid, saturated sodium bicarbonate, dried over anhydrous magnesium sulfate, filtered and concentrated under vacuum to provide the α-keto amide 21.

In Scheme G, step c, the α-keto amide 21 is deprotected under conditions well known in the art as described by T. H. Green, "Protective Groups in Organic Synthesis", John Wiley and Sons, 1981, Chapter 7 to provide the deprotected α-keto amide 22. For example, when "Pg" is a t-butyloxycarbonyl (Boc), the α-keto amide 21 is dissolved in a suitable solvent, such as ethyl acetate, treated with excess hydrogen chloride (gas) and stirred at about 0° C. to 30° C. for about 30 minutes to 4 hours. The solvent is then removed under vacuum to provide the deprotected α-keto amide 22 as the HCl salt.

The deprotected α-keto amide 22 is then subjected to the reaction conditions described in Scheme B to provide the compounds of formula 23.

The following examples present typical syntheses. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C" refers to degrees Celsius; "mm Hg" refers to millimeters of mercury; "$\mu$L" refers to microliters; "$\mu$g" refers to micrograms; and "$\mu$M" refers to micromolar.

EXAMPLE 1

Preparation of L-Prolinamide, N-(4-methoxy-1,4-dioxobutyl)-L-alanyl-L-alanyl-N-[2-(acetyloxy)-3-methoxy-1-(1-methylethyl)-3-oxo-1-propenyl]-, (E)- and (Z)-mixture (SEQ. ID NO. 6)

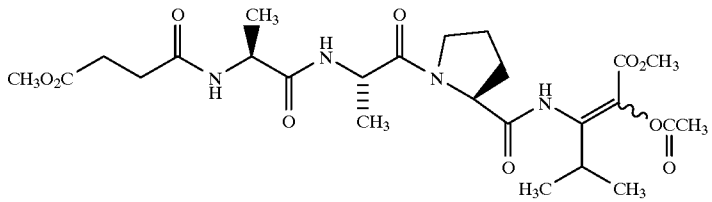

MDL 104,569

Scheme A; To pyridine (1.25 mL), stirred under N₂ and cooled to —20° C., add MeOSuc-Ala-Ala-Pro-Val-CO₂CH₃ (156 mg, 0.30 mmol) (Peet, N. P. et al., *J. Med. Chem.*, 33, 394 (1990); or Angelastro, M. R. et al., *J. Med. Chem.*, 33, 11 (1990)), followed several minutes later by acetic anhydride (0.29 mL, 3.0 mmol). Allow the reaction mixture to warm to room temperature and stir for 20 hours. Dilute the reaction mixture with CH₂Cl₂ (30 mL) and wash with 0.3 N HCl (2×20 mL) followed by brine (15 mL). Drying (MgSO₄), filtration, and concentration gives crude product.

Flash chromatography (4×14 cm silica gel column) eluting with a gradient (25 to 50%) of acetone in EtOAc gives the title compound (88 mg, 53%, ratio of E:Z isomers≈9:1) as a colorless oil.

¹H NMR (CDCl₃, 400 MHz) δ 10.16 (br s, 0.9H, CONHC=C of E isomer), 8.23 (br s, 0.1H, CONHC=C of Z isomer), 7.49 (br d, 0.1H, NH of Z isomer), 7.17 (br d, 0.9H, NH of E isomer), 6.50 (br d, 0.1H, NH of Z isomer), 6.43 (br d, 0.9H, NH of E isomer), 4.81–4.72 (m, 1.1H, CH of Ala for E isomer and CH of Ala for Z isomer and CH of Pro for Z isomer), 4.64 (t, 0.1H, CH of Ala for Z isomer), 4.58–4.48 (m, 1.8H, CH of Ala for E isomer and CH of Pro for E isomer), 3.76–3.63 (m, 2.7H, CH₂N of both isomers and 2× OCH₃ of Z isomer and CH of Z isomer), 3.42 (septet, 0.9H, CH of E isomer), 3.68 (S, 2.7H, OCH₃ of E isomer), 3.66 (s, 2.7H, OCH₃ of E isomer), 2.68–2.60 and 2.53–2.45 (pr m, 4H, COCH₂CH₂CO of both isomers), 2.22–1.95 (m, 4H, CH₂CH₂ of both isomers), 2.20 (s, 3H, CH₃CO of both isomers), 1.37 (d, 2.7H, CH₃ of Ala for E isomer), 1.32 (d, 2.7H, CH₃ of Ala for E isomer), 1.27 (d, 0.3H, CH₃ of Ala for Z isomer), 1.25 (d, 0.3H, CH₃ of Ala for Z isomer), 1.14 and 1.13 (pr d, 5.4H, 2× CH₃ of Val for E isomer), 1.05 and 1.02 (pr d, 0.6H, 2× CH₃ of Val for Z isomer).

MS (CI, CH₄) m/z (rel intensity) 555 (MH⁺, 62), 354 (38), 299 (100).

HRMS C₂₅H₃₉N₄O₁₀ (MH⁺) calcd 555.2666, obsd 555.2669.

EXAMPLE 2

Preparation of L-Prolinamide, N-[4-[[[(4-chlorophenyl)sulfonyl]amino]carbonyl]benzoyl]-L-valyl-N-[2-(acetyloxy)-3-methoxy-1-(1-methylethyl)-3-oxo-1-propenyl]-, (E)

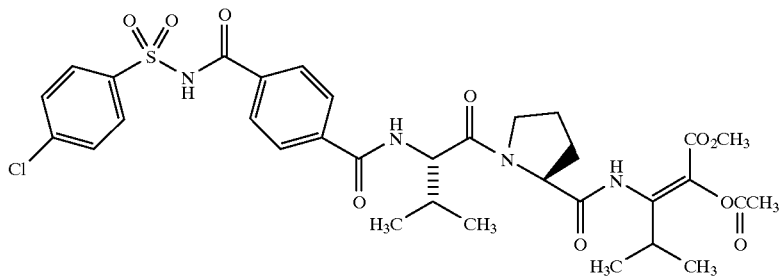

MDL 105,565

Scheme A; Treat N-(4-((4-chlorophenyl)sulfonylaminocarbonyl)phenylcarbonyl-Val-Pro-Val-CO₂CH₃ (135 mg, 0.20 mmol)(Mehdi, S. et al., *Biochem. Biophys. Res. Comm.*, 166, 595 (1990)) with acetic anhydride (0.19 mL, 2.0 mmol) in pyridine (1.0 mL) followed by preparative TLC (developed using EtOAc) in a manner analogous to the procedure described in Example 1 to give the title compound (23 mg, 16%) as a white foam.

¹H NMR (CDCl₃, 300 MHz) δ 10.40 (br s, 1H, CONHC=C), 8.11–8.05 (m, 2H, aryl), 7.78–7.71 (m, 2H, aryl), 7.71–7.63 (m, 2H, aryl), 7.55–7.49 (m, 2H, aryl), 7.24 (br d, 1H, NH of Val), 4.98 (dd, 1H, CH), 4.46 (dd, 1H, CH), 4.02–3.89 and 3.89–3.76 (pr m, 2H, CH₂N), 3.68 (s, 3H, OCH₃), 3.47 (septet, 1H, CHC=C), 2.39–1.96 (m, 5H, CH₂CH₂ and CH), 2.21 (s, 3H, CH₃CO), 1.17 and 1.16 and 1.07 and 0.94 (four d, 12H, 4× CH₃).

MS (CI, CH₄) m/z (rel intensity) 749 (1), 747 (M+C₂H₅⁺, 2), 721 (4), 719 (M⁺H, 10), 299 (100).

HRMS C₃₃H₄₀ClN₄O₁₀S (MH⁺) calcd 719.2154, obsd 719.2146.

EXAMPLE 3
Preparation of L-Prolinamide, N-[4-[[[(4-chlorohenyl) sulfonyl]amino]carbonyl]benzoyl]-L-valyl-N-[2-(acetyloxy)-3-amino-1-(1-methylethyl)-3-oxo-1-propenyl]-, (E)

c) Preparation of L-Prolinamide, N-[4-[[[(4-chlorophenyl) sulfonyl]amino]carbonyl]benzoyl]-L-valyl-N-[2-(acetyloxy)-3-amino-1-(1-methylethyl)-3-oxo-1-propenyl]-, (E)

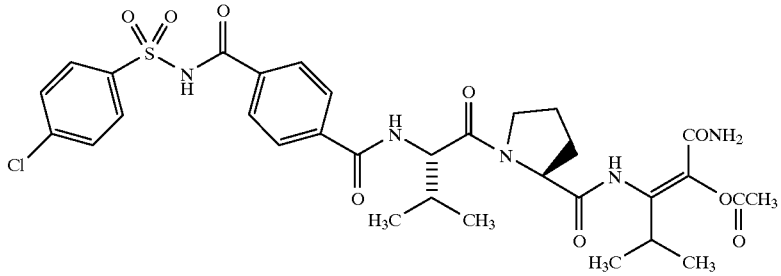

a) Preparation of N-(4-((4-chlorophenyl)-sulfonylaminocarbonyl)phenylcarbonyl-Val-Pro-Val-COOH Scheme G, step a; Dissolve N-(4-((4-chlorophenyl)-sulfonylaminocarbonyl)phenylcarbonyl-Val-Pro-Val-CO$_2$CH$_3$ (677 mg, 1.0 mmol) in a THF:methanol:water (1:1:1) solvent mixture (30 mL) and treat with 1.0 N aqueous lithium hydroxide (2.2 mL, 2.2 mmol). Stir the reaction mixture at 0° C. for 3 hours. Then, dilute the reaction mixture with ethyl acetate (100 mL), followed by an equal volume of water. After the layers are separated, slowly add 1N HCl (3 mL) to the aqueous layer and extract with ethyl acetate (3×25 mL). The combined organic extracts are dried over anhydrous magnesium sulfate, filtered and concentrated under vacuum to provide the title compound.

b) Preparation of N-(4-((4-chlorophenyl)-sulfonylaminocarbonyl)phenylcarbonyl-Val-Pro-Val-CONH$_2$ Scheme G, step b; Dissolve the product of Example 3(a) in methylene chloride (20 mL). Then add to the reaction mixture 1-hydroxybenzotiazole (68 mg, 0.5 mmol), diisopropylethylamine (0.17 mL, 1.0 mmol), and bubble in three equivalents of anhydrous ammonia (26 mg, 1.5 mmol). Subsequently add 1-(3-dimethylaminopropyl)-3-ethylcarbodiimide hydrochloride (96 mg, 0.5 mmol) to the reaction mixture and stir at a temperature of 0° C. for four hours. Dilute the reaction mixture with methylene chloride (10 mL), rinse with cold 0.5 N HCl (15 mL) and saturated sodium aqueous bicarbonate (15 mL). Then dry over anhydrous magnesium sulfate, filter and concentrate under vacuum to provide the title compound.

Scheme A; The product of Example 3(b) (141 mg, 0.20 mmol) is treated with acetic anhydride (0.19 mL, 2.0 mmol) in pyridine (1.0 mL) followed by preparative in a manner analogous to the procedure described in Example 1 to give the title compound.

EXAMPLE 4
Preparation of L-Prolinamide, N-[4-[[[(4-chlorophenyl) sulfonyl]amino]carbonyl]benzoyl]-L-valyl-N-[1-(1-methylethyl)-3-oxo-2-(acetyloxy)-3-(phenylamino)-1-propenyl]-, (E)

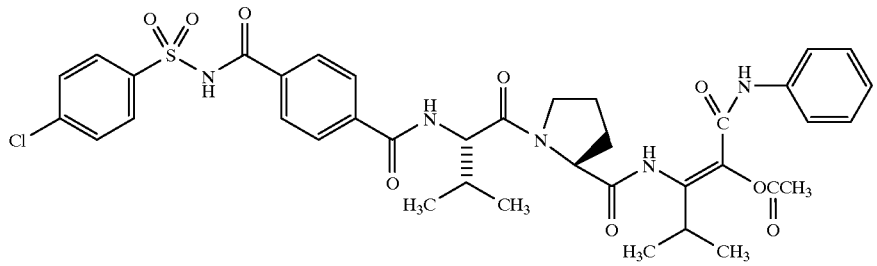

a) Preparation of N-(4-((4-chlorophenyl)-sulfonylaminocarbonyl)phenylcarbonyl-Val-Pro-Val-CONHC$_6$H$_5$ Scheme G, step b; Couple aniline (46 μL, 0.5 mmol) to the product of Example 3(a) in a manner analogous to the procedure of Example 3(b) to provide the title product.

b) Preparation of L-Prolinamide, N-[4-[[[(4-chlorophenyl) sulfonyl]amino]carbonyl]benzoyl]-L-valyl-N-[1-(1-methylethyl)-3-oxo-2-(acetyloxy)-3-(phenylamino)-1-propenyl]-, (E)

Scheme A; The product of Example 4(a) (156 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 5
Preparation of L-Prolinamide, N-acetyl-L-valyl-N-[2-(acetyloxy)-3-ethoxy-1-(1-methylethyl)-3-oxo-1-propenyl]-, (E)

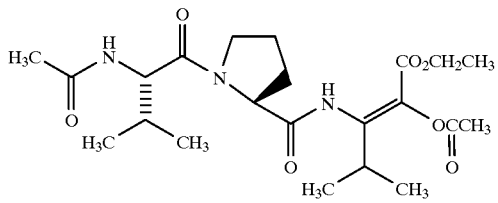

a) Preparation of Ethyl 3-Amino-2-hydroxy-4-methyl-pentanoate•hydrochloride

Treat 3-Amino-2-hydroxy-4-methylpentanoic acid (0.89 g, 6.05 mmol) (Peet, N. P. et al., *J. Med. Chem.*, 33, 394 (1990)) in $CH_3CH_2OH$ (25 mL and then 20 mL) with gaseous HCl. Concentrate and dry over KOH pellets to give the title compound.

b) Preparation of Ethyl 3-[(N-Acetyl-L-valyl-L-prolyl)amino]-2-hydroxy-4-methylpentanoate Cool a solution of NMM (0.22 mL, 2.00 mmol) and Ac-Val-Pro-OH (531 mg, 2.00 mmol) in $CH_3CN$ (20 mL) to −20° C. and add i-BuOCOCl (0.26 mL, 2.00 mmol). After 10 min, add a solution of the product of Example 5(a) (423 mg, 2.00 mmol) and N-methylmorpholine (0.22 mL, 2.0 mmol) in $CHCl_3$ (3 mL) and allow the reaction mixture to warm slowly to room temperature. After 2.5 hours, dilute the reaction mixture, with methylene chloride, wash with 0.5 N HCl (2×15 mL) and saturated aqueous $NaHCO_3$ (2×15 mL). Dry ($MgSO_4$), filter and concentrate to give crude product. Flash chromatograph to give the title compound.

c) Preparation of N-Acetyl-L-valyl-N-[3-ethoxy-1-(1-methylethyl)-2,3-dioxopropyl]-L-prolinamide To a stirred solution of oxalyl chloride (0.12 mL, 1.43 mmol) in $CH_2Cl_2$ (1.5 mL), cooled to −60° C., add DMSO (0.20 mL, 2.86 mmol) in $CH_2Cl_2$ (0.5 mL). After 5 min, add the product of Example 5(b) (298 mg, 0.72 mmol) in $CH_2C_2$ (1.5 mL). Continue stirring for 25 min at −60° C. After adding $Et_3N$ (0.50 mL, 3.58 mmol), allow the mixture to warm to room temperature and apply directly to a column for flash chromatography. Combine and concentrate product-containing fractions to give the title compound.

d) Preparation of L-Prolinamide, N-acetyl-L-valyl-N-[2-(acetyloxy)-3-ethoxy-1-(1-methylethyl)-3-oxo-1-propenyl]-, (E)

Scheme A; The product of Example 5(c) (83 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 6

Preparation of L-Prolinamide, N-acetyl-L-prolyl-L-valyl-N-[2-(acetyloxy)-3-methoxy-1-(1-methylethyl)-3-oxo-1-propenyl]-, (E)- (SEQ. ID NO. 7)

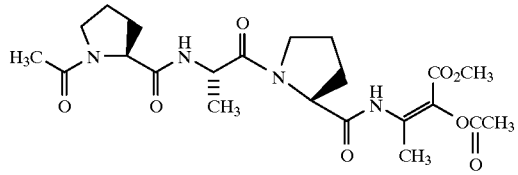

Scheme A; Treat N-Acetyl-L-prolyl-L-alanyl-N-(3-methoxy-1-methyl-2,3-dioxopropyl)-L-prolinamide (88 mg, 0.20 mmol)(Peet, N. P. et al.,*J. Med. Chem.*, 33, 394 (1990)) with acetic anhydride (0.19 mL, 2.0 mmol) in pyridine (1.0 mL) followed by preparative TLC in a manner analogous to the procedure described in Example 1 to give the title compound.

EXAMPLE 7

Preparation of L-Prolinamide. N-[4-(4-morpholinylcarbonyl)benzoyl]-L-valyl-N-[2-(acetyloxy)-3-ethoxy-1-(1-methylethyl)-3-oxo-1-propenyl]-, (E)

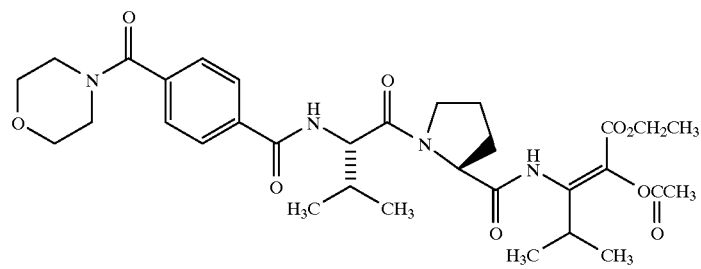

a) Preparation of Ethyl 3-[(N-Boc-L-valyl-L-prolyl)amino]-2-hydroxy-4-methylpentanoate Couple Boc-Val-Pro-OH (630 mg, 2.00 mmol) to the product of Example 5(a) (423 mg, 2.00 mmol) in a manner analagous to the procedure described in Example 5(b) to give the title compound.

b) Preparation of N-Boc-L-valyl-N-[3-ethyloxy-1-(1-methylethyl)-2,3-dioxopropyl]-L-prolinamide Oxidize the product of Example 7(a) (338 mg, 0.72 mmol) in a manner analogous to the procedure described in Example 5(c) to give the title compound.

c) Preparation of N-L-valyl-N-[3-ethyloxy-1-(1-methylethyl)-2,3-dioxopropyl]-L-prolinamide Hydrochloride Salt Bubble HCl gas through a cold (0° C.) solution the product of Example 7(b) (0.94 g, 2.00 mmol) in EtOAc (50 mL) for 5 min. Stir the reaction mixture at 0° C. for 1.5 h, and remove the solvents in vacuo to provide the title compound which is used without further purification.

d) Preparation of N-[4-(4-Morpholinylcarbonyl)benzoyl]-L-valyl-N-[3-ethoxy-1-(1-methylethyl)-2,3-dioxopropyl]-L-prolinamide To a stirred suspension of 4-(4-morpholinylcarbonyl)-benzoic acid (235 mg, 1.0 mmol) (Angelastro, M. R. et al., *J. Med. Chem.*, 37, 4538 (1994)) and benzyltriethylammonium chloride (2 mg) in 1,2-dichloroethane (5 mL) add thionyl chloride (88 μL, 1.2 mmol) and heat to reflux. After 19 h, allow the solution to cool to room temperature and concentrate to give the acid chloride as a light orange liquid, which is used without further purification. In a separate flask, cool a stirred solution of the product of Example 7(c) (406 mg, 1.0 mmol) in $CH_2Cl_2$ (10 mL) to −20° C. Add NMM (0.33 mL, 3.0 mmol) immediately followed by the addition of a solution of the acid chloride in $CH_2Cl_2$ (5 mL) at such a rate as to maintain the internal reaction temperature at −13° C. or less. After the addition is complete, allow the reaction mixture to warm to room temperature. After an additional 2 h, dilute the reaction mixture with $CH_2Cl_2$ (20 mL) and wash with 0.5 N HCl (2×15 mL), saturated $NaHCO_3$ (2×15 mL), and brine (15 mL).

Drying and concentration gives crude title compound. Flash chromatography gives the title compound.

e) Preparation of L-Prolinamide, N-[4-(4-morpholinylcarbonyl)benzoyl]-L-valyl-N-[2-(acetyloxy)-3-ethoxy-1-(1-methylethyl)-3-oxo-1-propenyl]-, (E)

Scheme A; The product of Example 7(d) (117 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 8

Preparation of L-Prolinamide, N-(4-morpholinylcarbonyl)-L-valyl-N-[2-(acetyloxy)-3-ethoxy-1-(1-methylethyl)-3-oxo-1-propenyl]-, (E)

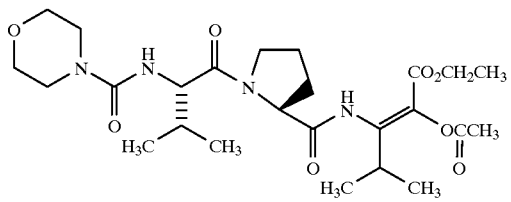

a) Preparation of N-(4-Morpholinylcarbonyl)-L-valyl-N-[3-ethoxy-1-(1-methylethyl)-2,3-dioxopropyl]-L-prolinamide To a solution of the product of Example 7(c) (406 mg, 1.0 mmol) in $CH_2Cl_2$ (20 mL), add 4-morpholinecarbonyl chloride (0.47 mL, 4.0 mmol) and NMM (0.55 mL, 5.0 mmol). Stir the mixture for 2.5 h, concentrate the solvent and purify the residue by flash chromatography to provide the title compound.

b) Preparation of L-Prolinamide, N-[4-(4-morpholinylcarbonyl)benzoyl]-L-valyl-N-[2-(acetyloxy)-3-ethoxy-1-(1-methylethyl)-3-oxo-1-propenyl]-, (E)

Scheme A; The product of Example 8(a) (97 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 9

Preparation of L-Prolinamide, N-(2-furoyl)-L-valyl-N-[2-(acetyloxy)-3-ethoxy-1-(1-methylethyl)-3-oxo-1-propenyl]-, (E)

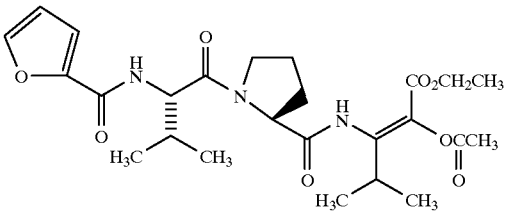

a) Preparation of N-(2-Furoyl)-L-valyl-N-[3-ethyloxy-1-(1-methylethyl)-2,3-dioxopropyl]-L-prolinamide Couple 2-furoyl chloride (0.10 mL, 1.0 mmol) with the product of Example 7(c) (406 mg, 1.0 mmol) in the presence of NMM (0.33 mL, 3.0 mmol) in a manner analogous to the procedure of Example 8(a) to provide the title compound.

b) Preparation of L-Prolinamide, N-(2-furoyl)-L-valyl-N-[2-(acetyloxy)-3-ethoxy-1-(1-methylethyl)-3-oxo-1-propenyl]-, (E)

Scheme A; The product of Example 9(a) (93 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 10

Preparation of L-Prolinamide, N-[(tetrahydro-2H-pyran-4-yl)carbonyl]-L-valyl-N-[2-(acetyloxy)-3-ethoxy-1-(1-methylethyl)-3-oxo-1-propenyl]-, (E)

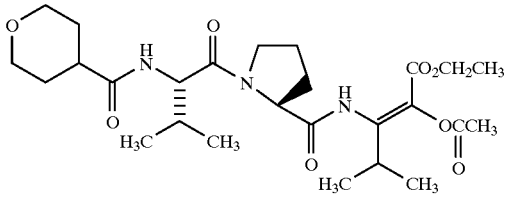

a) Preparation of N-[(Tetrahydro-2H-pyran-4-yl)carbonyl]-L-valyl-N-[3-ethyloxy-1-(1-methylethyl)-2,3-dioxopropyl]-L-prolinamide To a mixture of tetrahydro-2H-pyran-4-carboxylic acid (130 mg, 1.0 mmol) (Angelastro, M. R. et al, *J. Med. Chem.*, 37, 4538 (1994)) and DMF (0.1 mL) in $CH_2Cl_2$ is added oxalyl chloride (1.0 mmol, 87 μL). Stir the mixture at room temperature for 0.5 h, followed by the addition of NMM (3.0 mmol, 0.33 mL) and the product of Example 7(c) (406 mg, 1.0 mmol). Stir the mixture for 2.5 h, pour into $H_2O$ and extract with methylene chloride. Combine, dry ($MgSO_4$) and concentrate the extracts. Purify the residue by flash chromatography to yield the title compound.

b) Preparation of L-Prolinamide, N-[(tetrahydro-2H-pyran-4-yl)carbonyl]-L-valyl-N-[2-(acetyloxy)-3-ethoxy-1-(1-methylethyl)-3-oxo-1-propenyl]-, (E)

Scheme A; The product of Example 10(a) (96 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 11
Preparation of L-Prolinamide, N-[3-(4-morpholinyl)-1,3-dioxopropyl]-L-valyl-N-[2-(acetyloxy)-3-ethoxy-1-(1-methylethyl)-3-oxo-1-propenyl]-, (E)

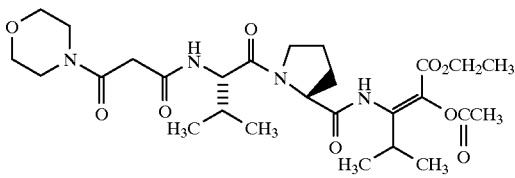

a) Preparation of N-[3-(4-Morpholinyl)-1,3-dioxopropyl]-L-valyl-N-[3-ethyloxy-1-(1-methylethyl)-2,3-dioxopropyl]-L-prolinamide Activate 2-(4-morpholinylcarbonyl)ethanoic acid (173 mg, 1.0 mmol) (Angelastro, M. R. et al., *J. Med. Chem.*, 37 4538, (1994)) with oxalyl chloride (87 μL, 1.0 mmol) and couple with the product of Example 7(c) (406 mg, 1.0 mmol) in the presence of NMM (0.33 mL, 3.0 mmol) in a manner analogous to the procedure described in Example 10 (a). Purification by flash chromatography provides the title compound.

b) Preparation of L-Prolinamide, N-[3-(4-morpholinyl)-1,3-dioxopropyl]-L-valyl-N-[2-(acetyloxy)-3-ethoxy-1-(1-methylethyl)-3-oxo-1-propenyl]-, (E)

Scheme A; The product of Example 11(a) (105 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 12
Preparation of L-Prolinamide, N-[3-(3-pyridyl)propanoyl]-L-valyl-N-[2-(acetyloxy)-3-ethoxy-1-(1-methylethyl)-3-oxo-1-propenyl]-, (E)

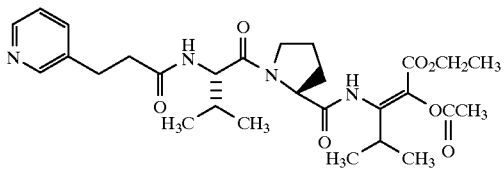

a) Preparation of N-[3-(3-Pyridyl)propanoyl]-L-valyl-N-[3-ethyloxy-1-(1-methylethyl)-2,3-dioxopropyl]-L-prolinamide To a suspension of 3-(3-pyridyl)propionic acid (302 mg, 2.0 mmol) (Walker, F. A. et al, *J. Am. Chem. Soc.*, 102, 5530 (1980)) in CH$_2$Cl$_2$ (30 mL), add Et$_3$N (0.84 mL, 6.0 mmol) and cool the resulting solution to –22° C. Add IBCF (0.26 mL, 2.0 mmol) and stir the reaction mixture for 20 min. Add additional Et$_3$N (0.28 mL, 2.0 mmol) followed by the addition the product of Example 7(c) (812 mg, 2.0 mmol) in one portion. After stirring for –22° C. for 4 h, concentrate the reaction mixture and purify by flash chromatography to give the title compound.

b) Preparation of L-Prolinamide, N-[3-(3-pyridyl) propanoyl]-L-valyl-N-[2-(acetyloxy)-3-ethoxy-1-(1-methylethyl)-3-oxo-1-propenyl]-, (E)

Scheme A; The product of Example 12(a) (101 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 13
Preparation of Glycinamide, N-(4-methoxy-1,4-dioxobutyl)-L-valyl-N-[2-(acetyloxy)-3-methoxy-1-(1-methylethyl)-3-oxo-1-propenyl-N$^2$-(2,3-dihydro-1H-inden-2-yl)-, (E)

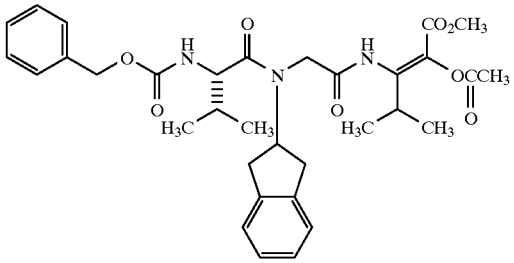

a) Preparation of CBZ-Val-N-(2,3-dihydro-1H-inden-2-yl) Gly-Val(OH)—CO$_2$CH$_3$ Couple N-(Carbobenzyloxy)-L-valyl-N-(2,3-dihydro-1H-inden-2-yl)glycine (425 mg, 1.0 mmol) (Skiles, J. W. et al., *J. Med. Chem.*, 35, 641 (1992)) to methyl 3-amino-2-hydroxy-4-methylpentanoate (161 mg, 1.0 mmol) (Peet, N. P. et al., *J. Med. Chem.*, 33, 394 (1990)) in a manner analogous to the procedure of Example 5(b) to provide the title compound.

b) Preparation of CBZ-Val-N-(2,3-dihydro-1H-inden-2-yl) Gly-Val-CO$_2$CH$_3$

The title compound is prepared from the product of Example 13(a) (284 mg, 0.5 mmol) following the oxidation procedure described in Example 5(c).

c) Preparation of Glycinamide, N-(4-methoxy-1,4-dioxobutyl)-L-valyl-N-[2-(acetyloxy)-3-methoxy-1-(1-methylethyl)- 3-oxo-1-propenyl-N$^2$-(2,3-dihydro-1H-inden-2-yl)-, (E)

Scheme A; The product of Example 13(b) (113 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 14
Preparation of Glycinamide, N-(4-methoxy-1,4-dioxobutyl)-L-valyl-N-[2-(acetyloxy)-3-methoxy-1-(1-methylethyl)-3-oxo-1-propenyl-N$^2$-methyl-, (E)

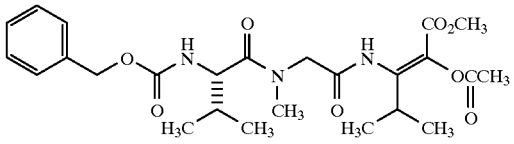

a) Preparation of CBZ-Val-N-(methyl)Gly-Val(OH)-CO$_2$CH$_3$

Couple N-(Carbobenzyloxy)-L-valyl-N-(methyl)glycine (322 mg, 1.0 mmol) (Skiles, J. W. et al., *J. Med. Chem.*, 35, 641 (1992)) to methyl 3-amino-2-hydroxy-4-methylpentanoate (161 mg, 1.0 mmol) (Peet, N. P. et al., *J. Med. Chem.*, 33, 394 (1990)) in a manner analogous to the procedure of Example 5(b) to provide the title compound.

b) Preparation of CBZ-Val-N-(2,3-dihydro-1H-inden-2-yl) Gly-Val-CO$_2$CH$_3$

The title compound is prepared from the product of Example 14(a) (233 mg, 0.5 mmol) following the oxidation procedure described in Example 5(c).

c) Preparation of Glycinamide, N-(4-methoxy-1,4-dioxobutyl)-L-valyl-N-[2-(acetyloxy)-3-methoxy-1-(1-methylethyl)-3-oxo-1-propenyl-M-methyl-, (E)

Scheme A; The product of Example 14(b) (93 mg, 0.20 mmol) is treated with acetic anhydride (0.19 mL, 2.0 mmol) in pyridine (1.0 mL) followed by preparative TLC in a manner analogous to the procedure described in Example 1 to give the title compound.

EXAMPLE 15

Preparation of L-Prolinamide, N-(4-methoxy-1,4-dioxobutyl)-L-alanyl-L-alanyl-N-[2-(acetyloxy)-3-methoxy-1-(1-methylethyl)-3-oxo-1-prolenyl]-, (Z)-(SEQ. ID NO. 8)

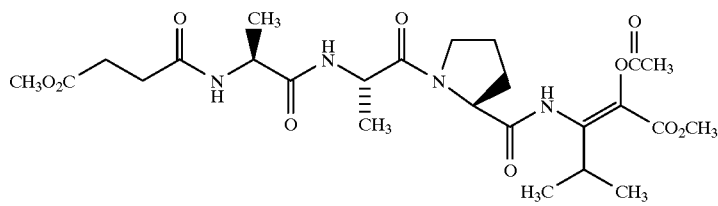

Scheme A; To a stirred solution of pyridine (1.25 mL) and MeOSuc-Ala-Ala-Pro-Val-CO$_2$CH$_3$ (156 mg, 0.30 mmol) under N$_2$ atmosphere and heated to reflux, add acetic anhydride (0.29 mL, 3.0 mmol) dropwise. After 30 min at reflux, cool the reaction mixture, dilute the reaction mixture with CH$_2$Cl$_2$ (30 mL) and wash with 0.3 N HCl (2×20 mL) followed by brine (15 mL). Drying (MgSO$_4$), filtration and concentration gives crude product. Flash chromatography eluting with a gradient (25 to 50%) of acetone in EtOAc gives the title compound.

EXAMPLE 16

Preparation of L-Prolinamide, N-(4-methoxy-1,4-dioxobutyl)-L-alanyl-L-alanyl-N-[2-(1-oxopropoxy)-3-methoxy-1-(1-methylethyl)-3-oxo-1-propenyl]-, (E)-(SEQ. ID NO. 9)

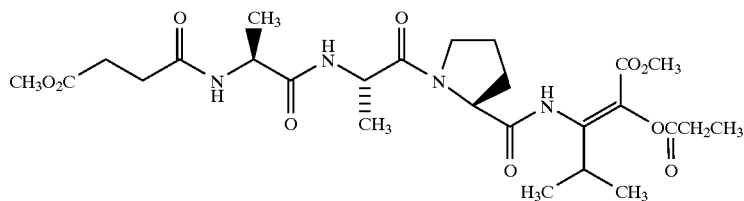

Scheme A; MeOSuc-Ala-Ala-Pro-Val-CO$_2$CH$_3$ (103 mg, 0.20 mmol) is treated with propionic anhydride (0.26 mL, 2.0 mmol) in pyridine (1.0 mL) followed by preparative TLC in a manner analogous to the procedure described in Example 1 to give the title compound.

EXAMPLE 17

Preparation of L-Prolinamide, N-(4-methoxy-1,4-dioxobutyl)-L-alanyl-L-alanyl-N-[2-(2-methyl-1-oxopropoxy)-3-methoxy-1-(1-methylethyl)-3-oxo-1-propenyl]-, (E)-(SEQ. ID NO. 10)

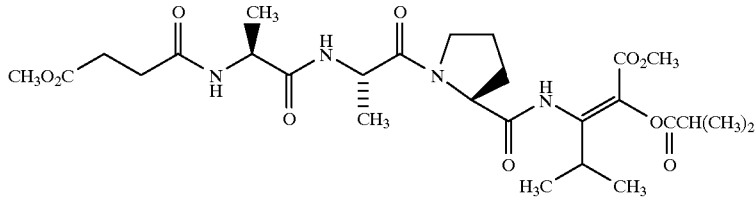

Scheme A; Treatment of MeOSuc-Ala-Ala-Pro-Val-CO$_2$CH$_3$ (103 mg, 0.20 mmol) with isobutyric anhydride (0.33 mL, 2.0 mmol), in pyridine (1.0 mL) followed by preparative TLC in a manner analogous to the procedure described in Example 1 yields the title compound.

Preferred embodiments of the subject compounds of the present invention are best realized in the compounds of Formulae I or IA wherein $R_1$ is isopropyl or n-propyl; preferably isopropyl; $R_2$ is $(C_1-C_4)$alkyl or phenyl; preferably $(C_1-C_4)$alkyl; $R_3$ is $(C_1-C_4)$alkyl or phenyl; preferably $(C_1-C_4)$alkyl; $P_2$ is Pro, Pip, Aze, Pro(4-OBzl) or Gly where the nitrogen of the α-amino group is substituted with an R group where R is $(C_1-C_6)$alkyl, phenyl, benzyl, cyclohexyl, cyclohexylmethyl, cyclooctyl, 2-bicyclo[2.2.1]-hexyl, morpholinyl, piperidinyl, pyridinyl or tetrahydroquinoline, preferably Pro; $P_3$ is Ile, Val or Ala; $P_4$ is Ala or is deleted and K is acetyl, t-butyloxycarbonyl, succinyl, methyoxysuccinyl, 4-((chlorophenyl)sulfonylaminocarbonyl)-phenylcarbonyl, or is a group of the formula

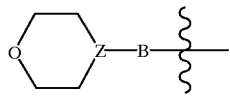

wherein Z is N or CH, B is a group of the formulae

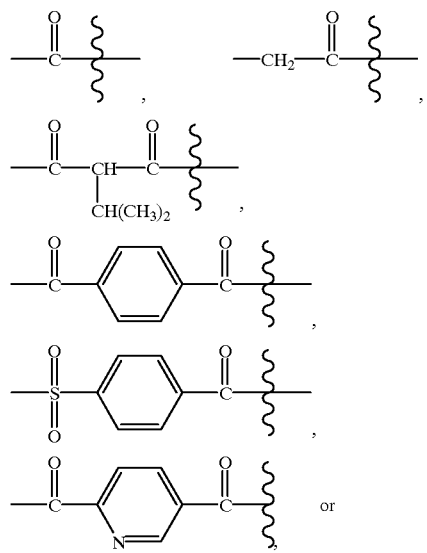

-continued

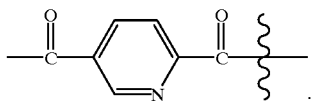

Specific examples of preferred compounds include:

L-Prolinamide, N-(4-methoxy-1,4-dioxobutyl)-L-alanyl-L-alanyl-N-[2-(acetyloxy)-3-methoxy-1-(1-methylethyl)-3-oxo-1-propenyl]-, (E)-; (SEQ. ID NO. 6)

L-Prolinamide, N-(4-methoxy-1,4-dioxobutyl)-L-alanyl-L-alanyl-N-[2-(acetyloxy)-3-methoxy-1-(1-methylethyl)-3-oxo-1-propenyl]-, (Z)-; (SEQ. ID NO. 8)

L-Prolinamide, N-(4-methoxy-1,4-dioxobutyl)-L-isoleucyl-N-[2-(acetyloxy)-3-methoxy-1-(1-methylethyl)-3-oxo-1-propenyl]-, (E)-;

L-Prolinamide, N-(4-methoxy-1,4-dioxobutyl)-L-valyl-N-[2-(acetyloxy)-3-methoxy-1-propyl-3-oxo-1-propenyl]-, (E)-;

L-Prolinamide, N-[4-[[[(4-chlorophenyl)sulfonyl]amino]carbonyl]benzoyl]-L-valyl-N-[2-(acetyloxy)-3-methoxy-1-(1-methylethyl)-3-oxo-1-propenyl]-, (E)-;

L-Prolinamide, N-[4-[[[(4-chlorophenyl)sulfonyl]amino]carbonyl]benzoyl]-L-valyl-N-[2-(acetyloxy)-3-methoxy-1-(1-methylethyl)-3-oxo-1-propenyl]-, (Z)-;

L-Prolinamide, N-[4-[[[(4-chlorophenyl)sulfonyl]amino]carbonyl]benzoyl]-L-valyl-N-[2-(acetyloxy)-3-amino-1-(1-methylethyl)-3-oxo-1-propenyl]-, (E)-;

L-Prolinamide, N-[4-[[[(4-chlorophenyl)sulfonyl]amino]carbonyl]benzoyl]-L-valyl-N-[2-(acetyloxy)-3-amino-1-(1-methylethyl)-3-oxo-1-propenyl]-, (Z)-;

L-Prolinamide, N-[4-[[[(4-chlorophenyl)sulfonyl]amino]carbonyl]benzoyl]-L-valyl-N-[1-(1-methylethyl)-3-oxo-2-(acetyloxy)-3-(phenylamino)-1-propenyl]-, (E)-;

L-Prolinamide, N-acetyl-L-valyl-N-[2-(acetyloxy)-3-ethoxy-1-(1-methylethyl)-3-oxo-1-propenyl]-, (E) -;

L-Prolinamide, N-acetyl-L-valyl-N-[2-(acetyloxy)-3-ethoxy-1-(1-methylethyl)-3-oxo-1-propenyl]-, (Z)-;

L-Prolinamide, N-acetyl-L-lysyl-N-[2-(acetyloxy)-3-ethoxy-1-(1-methylethyl)-3-oxo-1-propenyl]-, (E)-;

L-Prolinamide, N-acetyl-L-prolyl-L-valyl-N-[2-(acetyloxy)-3-methoxy-1-(1-methylethyl)-3-oxo-1-propenyl]-, (E)-; (SEQ. ID NO. 7)

L-Prolinamide, N-[4-(4-morpholinylcarbonyl)benzoyl]-L-valyl-N-[2-(acetyloxy)-3-ethoxy-1-(1-methylethyl)-3-oxo-1-propenyl]-, (E) -;

L-Prolinamide, N-[4-(4-morpholinylcarbonyl)benzoyl]-L-valyl-N-[2-(acetyloxy)-3-ethoxy-1-(1-methylethyl)-3-oxo-1-propenyl]-, (Z)-;

L-Prolinamide, N-(4-morpholinylcarbonyl)-L-valyl-N-[2-(acetyloxy)-3-ethoxy-1-(1-methylethyl)-3-oxo-1-propenyl]-, (E)-;
L-Prolinamide, N-(4-morpholinylcarbonyl)-L-valyl-N-[2-(acetyloxy)-3-ethoxy-1-(1-methylethyl)-3-oxo-1-propenyl]-, (Z) -;
L-Prolinamide, N-(2-furoyl)-L-valyl-N-[2-(acetyloxy)-3-ethoxy-1-(1-methylethyl)-3-oxo-1-propenyl]-, (E) -;
L-Prolinamide, N-[(tetrahydro-2H-pyran-4-yl)carbonyl]-L-valyl-N-[2-(acetyloxy)-3-ethoxy-1-(1-methylethyl)-3-oxo-1-propenyl]-, (E)
L-Prolinamide, N-[3-(4-morpholinyl)-1,3-dioxopropyl]-L-valyl-N-[2-(acetyloxy)-3-ethoxy-1-(1-methylethyl)-3-oxo-1-propenyl]-, (E)-;
L-Prolinamide, N-[3-(3-pyridyl)propanoyl]-L-valyl-N-[2-(acetyloxy)-3-ethoxy-1-(1-methylethyl)-3-oxo-1-propenyl]-, (E) -;
Glycinamide, N-(4-methoxy-1,4-dioxobutyl)-L-valyl-N-[2-(acetyloxy)-3-methoxy-1-(1-methylethyl)-3-oxo-1-propenyl-d-(2,3-dihydro-1H-inden-2-yl)-, (E)-;
Glycinamide, N-(4-methoxy-1,4-dioxobutyl)-L-valyl-N-[2-(acetyloxy)-3-methoxy-1-(1-methylethyl)-3-oxo-1-propenyl-d-(2,3-dihydro-1H-inden-2-yl)-, (Z)-;
Glycinamide, N-(4-methoxy-1,4-dioxobutyl)-L-valyl-N-[2-(acetyloxy)-3-methoxy-1-(1-methylethyl)-3-oxo-1-propenyl-$N^2$-methyl-, (E)-;
Glycinamide, N-(4-methoxy-1,4-dioxobutyl)-L-valyl-N-[2-(acetyloxy)-3-methoxy-1-(1-methylethyl)-3-oxo-1-propenyl-d-methyl-, (Z)-;
Glycinamide, N-(4-methoxy-1,4-dioxobutyl)-L-valyl-N-[2-(acetyloxy)-3-methoxy-1-(1-methylethyl)-3-oxo-1-propenyl-$N^2$-cyclopentyl-, (E) -;
Glycinamide, N-(4-methoxy-1,4-dioxobutyl)-L-valyl-N-[2-(acetyloxy)-3-methoxy-1-(1-methylethyl)-3-oxo-1-propenyl-d-cyclooctyl-, (E)-;
Glycinamide, N-(4-methoxy-1,4-dioxobutyl)-L-valyl-N-[2-(acetyloxy)-3-methoxy-1-(1-methylethyl)-3-oxo-1-propenyl-N-benzyl-, (E)-;
L-Prolinamide, N-(4-methoxy-1,4-dioxobutyl)-L-alanyl-L-alanyl-N-[2-(1-oxopropoxy)-3-methoxy-1-(1-methylethyl)-3-oxo-1-propenyl]-, (E) -;
L-Prolinamide, N-(4-methoxy-1,4-dioxobutyl)-L-alanyl-L-alanyl-N-[2-(2-methyl-1-oxopropoxy)-3-methoxy-1-(1-methylethyl)-3-oxo-1-propenyl]-, (E)-;
L-4-Thiazolidamide, N-(4-methoxy-1,4-dioxobutyl)-L-valyl-N-[2-(acetyloxy)-3-methoxy-1-(1-methylethyl)-3-oxo-1-propenyl]-, (E)-;
L-4-Thiazolidamide, N-[(1,1-dimethylethoxy)carbonyl]-L-valyl-N-[2-(acetyloxy)-3-methoxy-1-(1-methylethyl)-3-oxo-1-propenyl]-, (E) -;
L-1,2,3,4-Tetrahydro-3-isoquinolinamide, N-(4-methoxy-1,4-dioxobutyl)-L-valyl-N-[2-(acetyloxy)-3-methoxy-1-(1-methylethyl)-3-oxo-1-propenyl]-, (E)-; and
L-1,2,3,4-Tetrahydro-3-isoquinolinamide, N-[(1,1-dimethylethoxy)carbonyl]-L-valyl-N-[2-(acetyloxy)-3-methoxy-1-(1-methylethyl)-3-oxo-1-propenyl]-, (E)-.

In a further embodiment, the present invention provides a method for the treatment of a patient afflicted with a neutrophil associated inflammatory disease comprising the administration thereto of a therapeutically effective amount of a compound of formula I. The term "neutrophil associated inflammatory disease" refers to diseases or conditions characterized by the migration of neutrophils to the site of inflammation and its participation in proteolytic degradation of biological matrices. Neutrophil associated inflammatory diseases for which treatment with a compound of formula I will be particularly useful include: emphysema, cystic fibrosis, adult respiratory distress syndrome, septicemia, disseminated intravascular coagulation, gout, rheumatoid arthritis, chronic bronchitis and inflammatory bowel disease. Compounds of formula I which are particularly preferred for the treatment of neutrophil associated inflammatory diseases include:
L-Prolinamide, N-(4-methoxy-1,4-dioxobutyl)-L-alanyl-L-alanyl-N-[2-(acetyloxy)-3-methoxy-1-(1-methylethyl)-3-oxo-1-propenyl]-, (E)-; (SEQ. ID NO. 6)
L-Prolinamide, N-(4-methoxy-1,4-dioxobutyl)-L-alanyl-L-alanyl-N-[2-(acetyloxy)-3-methoxy-1-(1-methylethyl)-3-oxo-1-propenyl]-, (Z)-; (SEQ. ID NO. 8)
L-Prolinamide, N-[4-[[[(4-chlorophenyl)sulfonyl]amino]-carbonyl]benzoyl]-L-valyl-N-[2-(acetyloxy)-3-methoxy-1-(1-methylethyl)-3-oxo-l-propenyl]-, (E)-; and
L-Prolinamide, N-[4-[[[(4-chlorophenyl)sulfonyl]amino]-carbonyl]benzoyl]-L-valyl-N-[2-(acetyloxy)-3-methoxy-1-(1-methylethyl)-3-oxo-1-propenyl]-, (Z)-.

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

The term "therapeutically effective amount" refers to an amount which is effective, upon single or multiple dose administration to the patient, in providing relief of symptoms associated with neutrophil associated inflammatory diseases. As used herein, "relief of symptoms" of a respiratory disease refers to a decrease in severity over that expected in the absence of treatment and does not necessarily indicate a total elimination or cure of the disease. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula I is expected to vary from about 0.1 milligram per kilogram of body weight per day (mg/kg/day) to about 100 mg/kg/day. Preferred amounts are expected to vary from about 0.5 to about 10 mg/kg/day.

The compounds of this invention are prodrugs of highly potent inhibitors of elastase, particularly human neutrophil elastase or are inhibitors of elastase in their own right. It is believed that the compounds of this invention exert their inhibitory effect through inhibition of the enzyme elastase and thereby provide relief for elastase-mediated diseases including but not limited to emphysema, cystic fibrosis, adult rspiratory distress syndrome, septicemia, disseminated intravascular coagulation, gout, rheumatoid arthritis, chronic bronchitis and inflammatory bowel disease. However, it is understood that the present invention is not limited by any particular theory or proposed mechanism to explain its effectiveness in an end-use application.

In effecting treatment of a patient afflicted with a disease state described above, a compound of formula I can be administered in any form or mode which makes the compound bioavailable in effective amounts, including oral, aerosol, and parenteral routes. For example, compounds of formula I can be administered orally, by aerosolization, subcutaneously, intramuscularly, intravenously, transdermally, intranasally, rectally, topically, and the like. Oral or aerosol administration is generally preferred. One skilled in the art of preparing formulations can readily select the proper form and mode of administration depending upon the particular characteristics of the compound selected the disease state to be treated, the stage of the disease, and other relevant circumstances. Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formula I in admixture or otherwise in association with one or more inert carriers. These compositions are useful, for example, as assay standards, as convenient means of making bulk shipments, or as pharmaceutical compositions. An assayable amount of a compound of formula I is an amount which is readily measurable by standard assay procedures and techniques as are well known and appreciated by those skilled in the art. Assayable amounts of a compound of formula I will generally vary from about 0.001% to about 75% of the composition by weight. Inert carriers can be any material which does not degrade or otherwise covalently react with a compound of formula I. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula I in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula I of the present invention may also be administered by aerosol. The term aerosol is used to denote a variety of systems ranging from those of colloidal nature to systems consisting of pressurized packages. Delivery may be by a liquified or compressed gas or by a suitable pump system which dispenses the active ingredients. Aerosols of compounds of formula 1 may be delivered in single phase, bi-phasic, or tri-phasic systems in order to deliver the active ingredient. Delivery of the aerosol includes the necessary container, activators, valves, subcontainers, and the like. Preferred aerosol are able to be determined by one skilled in the art.

The compounds of formula I of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula 1 or its pharmaceutical salt from about 0.1 to about 10% w/v (weight per unit volume).

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

In vivo, the compounds of formula 1 are converted by esterases to compounds known to be active as human elastase inhibitors. For example, compounds of formula 1 are converted into compounds disclosed in European Pat. Appl. OPI No. 0195212, published Sep. 24, 1986 and Peet, N. P. et al., *J. Med. Chem.*, 33: 394–407 (1990) said references herein disclosed by reference as if fully set forth.

The activity of the compounds to inhibit elastase, or act as prodrugs of elastase inhibitors, and the usefulness of the compounds of Formulae I and IA in treating neutrophil associated inflammatory disease, can be demonstrated by well-recognized and reliable in vitro and in vivo models.

EXAMPLE 18

In vitro Assay of Elastase in the Presence of MDL 104,569 and Porcine Liver Esterase Elastase was assayed in vitro using the chromogenic substrate N-MeOSuc-Ala-Ala-Pro-Val-p-nitroanilide ([S]= 0.20 mM; Km=0.16 mM), available commercially. The assay techniques are similar to those described by Mehdi, et al., *Biochemical and Biophysical Research Communications*, 166, 595 (1990). The assay mixture consists of partially purified elastase and substrate (0.2 mM) in 0.1 M HEPES (pH 7.5), 0.5 M NaCl, 10% DMSO and 0.1% Brij 35. The reaction (1 or 2 mL, in a plastic cuvette) is maintained at 37° C. and the hydrolysis of the substrate is followed in the presence of MDL 104,569 and 5 units/mL of porcine liver esterase (Sigma Chemical Co., cat. no. E-3128). Elastase is isolated from human sputum, although recently it has become commercially available. The rate of hydrolysis of the substrate with no inhibitor or prodrug added is assigned 100%. In the presence of 1 $\mu$M MDL 104,569, a rate of 81% was obtained; when esterase (porcine kidney, Sigma Chemical Co.) was also present, the rate decreased to 24%. At a concentration of 10 $\mu$M, the rate observed from the final extent of inhibition in the assay in the presence of esterase was 130 nM, compared to a Ki of 200 nM for the parent drug measured independently.

EXAMPLE 19

In vitro Assay of Elastase in the Presence of MDL 105,565 and Porcine Liver Esterase Elastase was assayed in vitro in the presence of MDL 105,565 using the techniques and procedures described in Example 18. With MDL 105,565, at a concentration of 10 nM, a rate of 99% was obtained; when esterase was added, this rate was 76%. At a concentration of 45 nM, the rates were 94% (without esterase) and 37% (with esterase). In this case, the Ki of the liberated drug was calculated to be 13 nM, compared with a Ki of 2 nM determined independently.

EXAMPLE 20

HNE-Induced Lung Hemorrhage in Hamsters

Acute pulmonary damage induced by HNE is measured using a pulmonary hemorrhage model as described, for example, by Fletcher, D. S. et al., *Am. Rev. Respir. Dis.*, 141: 672–677 (1990); Skiles, J. W. et al., *J. Med. Chem.*, 35: 641–662 (1992); Shah, S. K. et al., *J. Med. Chem.*, 35: 3745–3754 (1992) or Durham, S. L. et al. *J. Pharm. Exo. Ther.*, 270: 185–191 (1994). HNE (10–25 $\mu$g/hamster in 0.05 M sodium acetate-buffered saline) is instilled (i.t.) as described previously by Schranfnagel, D. et al., *Am. Rev. Resp. Dis.*, 129: A324 (1984) to $CO_2$-anaesthetized Male Golden Syrian hamsters weighing 75 to 125 g (Charles River, Kingston, N.Y.). Instillation is performed using a blunt 20-gauge 3-inch stainless steel needle inserted into the trachea to a point before the trachea carina using a fiberoptic light source positioned on the larynx of the animal. The volume of HNE or vehicle is about 100 $\mu$L. The animals are euthanized by $CO_2$ asphyxiation 1 hr later and bled by cutting the inferior vena cava below the liver. The trachea is exposed and cannulated with PE-100 tubing (Clay Adams, Parsippany, N.J.) and the BAL fluid is collected by gently instilling and withdrawing a single volume of saline (0.04 mL of saline/g) three times. The hemoglobin content of the BAL fluid is determined using a spectrophotometric assay and quantitated relative to a Hgb standard curve. Results are expressed as milligrams per milliliter of Hgb±S.E.

Inhibition of HNE-induced lung hemorrhage is determined by dosing the hamsters p.o., i.v. or i.t. with a compound of Formulae I or IA before or after i.t. installation of HNE. The vehicles for dosing animals with the compounds of Formulae I or IA are 20% emulphor/water (p.o.), 0.2% triethylamine/saline (i.v.) and 10% dimethyl sulfoxide (i.t.). The appropriate vehicle controls are included in all experiments. Hamsters are dosed orally with drug or vehicle (5 mL/kg) using 20-gauge curved dosing needle attached to a 1 mL syringe (5 mL/kg). Intravenous injections (2 mL/kg) are performed via the jugular vein using a 26-gauge, ½ inch needle attached to a 1 mL syringe. Intratracheal administration of drug and vehicle is as described above for HNE installation.

What is claimed is:

1. A compound of the formulae

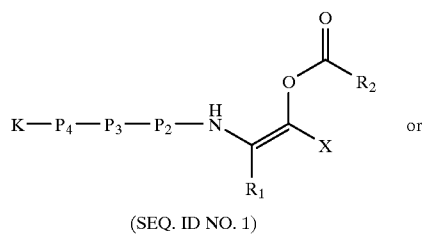

(SEQ. ID NO. 1)

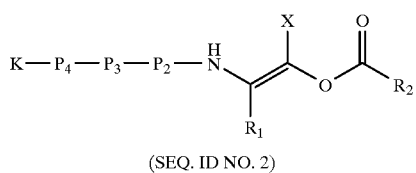

(SEQ. ID NO. 2)

wherein $R_1$ is methyl, propyl or isopropyl;

$R_2$ is $(C_1-C_4)$alkyl, phenyl, benzyl, cyclohexyl or cyclohexylmethyl;

X is —$CONHR'_3$, wherein $R_3'$ is hydrogen, $(C_1-C_4)$alkyl, phenyl, benzyl, cyclohexyl or cyclohexylmethyl;

$P_2$ is Gly or Ala where the nitrogen of the α-amino group is optionally substituted with an R group where R is $(C_1-C_6)$alkyl, $(C_3-C_{12})$cycloalkyl, cyclohexylmethyl, cyclopentylethyl, 2-bicyclo[1.1.0]butyl, 2-bicyclo[2.2.1]-hexyl, 2-bicyclo-hexylmethyl, phenyl, 1-naphthyl, 2-naphthyl, benzyl, morpholinyl, piperidinyl, morpholino-methyl, pyridinyl, 2-quinoxalinyl, quinolinyl, 3-quinolinylmethyl, 2-indanyl, or tetrahydroquinoline or $P_2$ is Pro, Aze, Tic, Pip, Tca, Pro(OBzl), Pro(4-OAc), or Pro(4-OH);

$P_3$ is Ala, Leu, Ile, Nle, Val, Nva, or Lys $P_4$ is Ala, bAla, Val, Nva, bVal, Pro or is deleted;

K is hydrogen, acetyl, succinyl, benzoyl, t-butyloxycarbonyl, carbobenzyloxy, dansyl, isovaleryl, methoxysuccinyl, 1-adamantanesulphonyl, 1-adamantaneacetyl, 2-carboxybenzoyl, —C(O)N(CH$_3$)$_2$, 4-((chlorophenyl)sulfonylaminocarbonyl)phenyl-carbonyl, 4-((4-bromophenyl)sulfonylaminocarbonyl)phenyl-carbonyl, 4-(sulfonylaminocarbonyl)phenylcarbonyl or is a group of the formulae

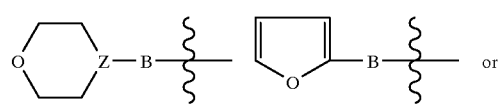

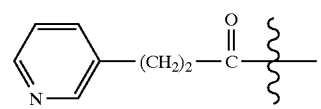

wherein Z is N or CH, B is a group of the formulae

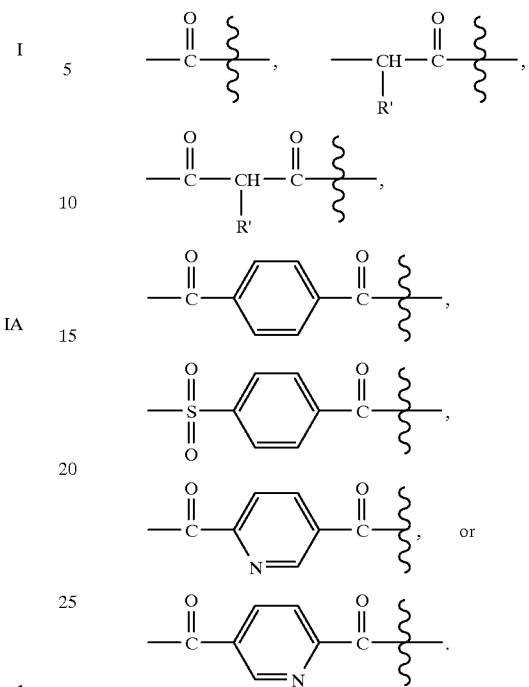

R' is a hydrogen or a $(C_1-C_4)$alkyl group;

n is zero or the integers 1 or 2;

or a hydrate or a pharmaceutically acceptable salt thereof.

2. A compound of claim 1 wherein $P_2$ is Gly or Ala where the nitrogen of the α-amino group is optionally substituted with an R group where R is methyl, cyclopentyl, or 2-indanyl or $P_2$ is Pro, Aze or Tic; $P_3$ is Ile, Val, or Ala; $P_4$ is Ala, Pro or is deleted; and K is acetyl, succinyl, t-butyloxycarbonyl, carbobenzyloxy, methoxysuccinyl, —C(O)N(CH$_3$)$_2$, 4-((chlorophenyl)sulfonylaminocarbonyl)phenyl-carbonyl, 4-((4-bromophenyl)sulfonylaminocarbonyl)phenyl-carbonyl, 4-(sulfonylaminocarbonyl)phenylcarbonyl or is a group of the formula

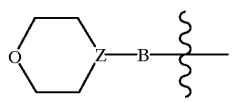

wherein Z is N or CH, B is a group of the formulae

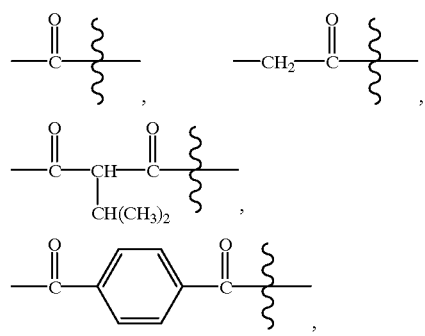

-continued

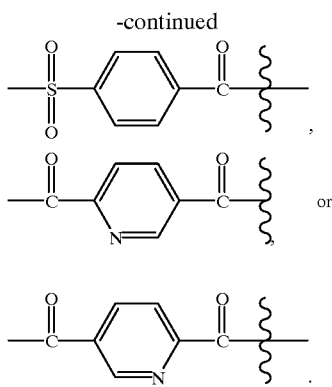, or

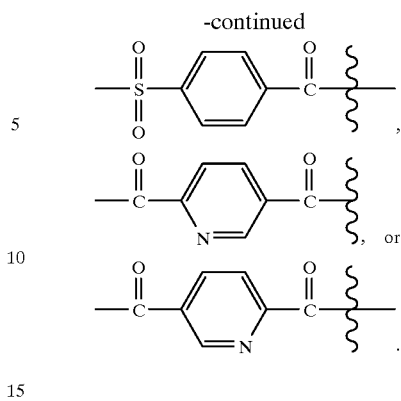, or

.

3. A compound of claim 2 wherein $R_1$ is isopropyl; $P_2$ is Pro; and K is acetyl, t-butyloxycarbonyl, succinyl, methoxysuccinyl, 4-((chlorophenyl)sulfonylaminocarbonyl)-phenylcarbonyl, or is a group of the formula

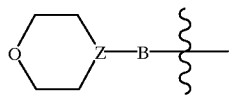

wherein Z is N or CH, B is a group of the formulae

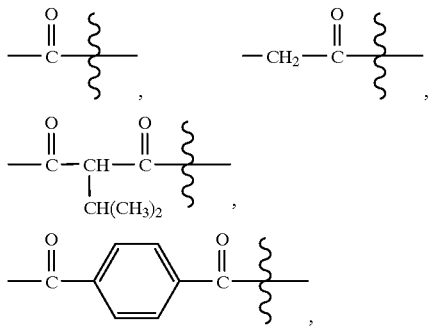

4. A compound of claim 1 wherein the compound is L-Prolinamide, N-(4-methoxy-1,4-dioxobutyl)-L-alanyl-L-alanyl-N-[2-(acetyloxy)-3-methoxy-1-(1-methylethyl)-3-oxo-1-propenyl]-, (E)-.

5. A compound of claim 1 wherein the compound is L-Prolinamide, N-[4-[[[(4-chlorophenyl)sulfonyl]amino]-carbonyl]benzoyl]-L-valyl-N-[2-(acetyloxy)-3-methoxy-1-(1-methylethyl)-3-oxo-1-propenyl]-, (E)-.

6. A composition comprising a compound of claim 1 and a carrier.

7. A pharmaceutical composition comprising a compound of claim 1 and a pharmaceutically acceptable carrier.

8. A method for inhibiting human neutrophil elastase in a patient in need thereof, said method comprising administering to the patient a therapeutically effective amount of a compound of claim 1.

9. A method of treating a patient afflicted with a neutrophil associated inflammatory disease, said method comprising administering to the patient a therapeutically effective amount of a compound of claim 1.

10. A method according to claim 9 wherein said neutrophil associated inflammatory disease is emphysema.

11. A method according to claim 9 wherein said neutrophil associated inflammatory disease is cystic fibrosis.

12. A method according to claim 9 wherein said neutrophil associated inflammatory disease is chronic obstructive pulmonary disorder.

* * * * *